(12) United States Patent
Schiffman et al.

(10) Patent No.: US 12,268,662 B2
(45) Date of Patent: Apr. 8, 2025

(54) FORMULATIONS COMPRISING CARBACHOL AND BRIMONIDINE TO ENHANCE ANTI- PRESBYOPIA EFFECTS

(71) Applicant: VISUS THERAPEUTICS, INC., Seattle, WA (US)

(72) Inventors: Rhett Schiffman, Seattle, WA (US); Bruce Firestone, Seattle, WA (US)

(73) Assignee: VISUS THERAPEUTICS, INC., Seattle, WA (US)

( * ) Notice: Subject to any disclaimer, the term of this patent is extended or adjusted under 35 U.S.C. 154(b) by 0 days.

(21) Appl. No.: 18/531,082

(22) Filed: Dec. 6, 2023

(65) Prior Publication Data

US 2024/0100009 A1 Mar. 28, 2024

Related U.S. Application Data

(63) Continuation of application No. PCT/US2022/079625, filed on Nov. 10, 2022.

(60) Provisional application No. 63/278,081, filed on Nov. 10, 2021.

(51) Int. Cl.
| | | |
|---|---|---|
| A61K 31/498 | (2006.01) | |
| A61K 9/00 | (2006.01) | |
| A61K 31/27 | (2006.01) | |
| A61K 47/38 | (2006.01) | |
| A61P 27/10 | (2006.01) | |

(52) U.S. Cl.
CPC ............ *A61K 31/27* (2013.01); *A61K 9/0048* (2013.01); *A61K 31/498* (2013.01); *A61K 47/38* (2013.01); *A61P 27/10* (2018.01)

(58) Field of Classification Search
None
See application file for complete search history.

(56) References Cited

U.S. PATENT DOCUMENTS

| | | |
|---|---|---|
| 8,299,079 B2 | 10/2012 | Kaufman |
| 8,455,494 B2 | 6/2013 | Kaufman |
| 2003/0036535 A1 | 2/2003 | Nolan |
| 2009/0156606 A1 | 6/2009 | Sharma |
| 2010/0173833 A1 | 7/2010 | Lajoie et al. |
| 2010/0298335 A1 | 11/2010 | Kaufman |
| 2011/0152274 A1* | 6/2011 | Kaufman ............ A61K 31/498 514/249 |
| 2012/0329805 A1 | 12/2012 | Kaufman |
| 2013/0245030 A1 | 9/2013 | Kaufman |
| 2014/0113946 A1 | 4/2014 | Abad |
| 2015/0065511 A1 | 3/2015 | Horn et al. |
| 2016/0250225 A1 | 9/2016 | Chang et al. |
| 2018/0078500 A1 | 3/2018 | Jiao et al. |
| 2019/0298738 A1* | 10/2019 | Bowman ................ A61K 47/34 |
| 2022/0175734 A1 | 6/2022 | Sambursky et al. |
| 2023/0210821 A1 | 7/2023 | Sambursky et al. |

FOREIGN PATENT DOCUMENTS

| | | | |
|---|---|---|---|
| CA | 2747095 C | 2/2020 | |
| JP | 2019031538 A | 2/2019 | |
| WO | WO-2011091225 A2 * | 7/2011 | ......... A61K 31/4184 |
| WO | WO-2014015183 A1 | 1/2014 | |
| WO | WO-2016172712 A2 | 10/2016 | |
| WO | WO-2016205068 A1 | 12/2016 | |
| WO | WO-2017160548 A1 | 9/2017 | |
| WO | WO-2018209051 A1 | 11/2018 | |
| WO | WO-2019104191 A1 | 5/2019 | |
| WO | WO-2020219707 A1 | 10/2020 | |
| WO | WO-2020252057 A1 | 12/2020 | |
| WO | WO-2020252061 A1 | 12/2020 | |
| WO | WO-2021021644 A1 | 2/2021 | |
| WO | WO-2021021646 A1 | 2/2021 | |
| WO | WO-2023086878 A1 | 5/2023 | |

OTHER PUBLICATIONS

International Search Report and Written Opinion for International Application No. PCT/US2020/037042, USPTO, mailed on Oct. 16, 2020, 20 pages.

Abdelkader, A., "Improved Presbyopic Vision With Miotics," Eye Contact Lens 41(5):323-7, Lippincott Williams and Wilkins Ltd., United States (Sep. 2015).

Abdelkader, A., "Influence of Different Concentrations of Carbachol Drops on the Outcome of Presbyopia Treatment—A Randomized Study," International Journal of Ophthalmic Research 5(1):317-320, ACT Publishing Group Limited, United Kingdom (2019).

Abdelkader, A., et al., "Clinical outcomes of combined versus separate carbachol and brimonidine drops in correcting presbyopia," Eye Vis (Lond) 3:31, BioMed Central, United Kingdom (Dec. 2016).

International Search Report and Written Opinion for International Application No. PCT/US2020/037046, USPTO, mailed on Oct. 26, 2020, 14 pages.

Abdelkader, A. "A Novel Pharmacological Treatment of Pseudophakic Presbyopia," International Journal of Ophthalmic Research 4(2): 291-294, ACT Publishing Group Limited, United Kingdom (2018).

International Search Report and Written Opinion for International Application No. PCT/US2021/057720, Commissioner for Patents, United States, mailed on Feb. 1, 2022, 16 pages.

International Search Report and Written Opinion for International Application No. PCT/US2022/079625, International Search Authority, United States, mailed on Mar. 3, 2023, 11 pages.

Chrai, S.S., and Robinson, J.R., "Ocular evaluation of methylcellulose vehicle in albino rabbits," J Pharm Sci 63(8):1218-1223, Wiley, United States (Aug. 1974).

Patton, T.F., and Robinson, J.R., "Ocular evaluation of polyvinyl alcohol vehicle in rabbits," J Pharm Sci 64(8):1312-1316, Wiley, United States (Aug. 1975).

* cited by examiner

Primary Examiner — Gigi G Huang
(74) Attorney, Agent, or Firm — Sterne, Kessler, Goldstein & Fox P.L.L.C.

(57) ABSTRACT

The present disclosure is directed to ophthalmic formulations comprising carbachol, processes for preparing ophthalmic formulations comprising carbachol, and methods of treating presbyopia and other ophthalmic conditions by administering ophthalmic formulations comprising carbachol to a subject in need thereof.

11 Claims, 12 Drawing Sheets

FORMULATIONS COMPRISING CARBACHOL AND BRIMONIDINE TO ENHANCE ANTI-PRESBYOPIA EFFECTS

REFERENCE TO RELATED APPLICATIONS

This application is a continuation application of International Application No. PCT/US2022/079625, filed Nov. 10, 2022, which claims priority to U.S. Provisional Application No. 63/278,081, filed Nov. 11, 2021, each of which is hereby incorporated by reference in its entirety.

FIELD AND BACKGROUND OF THE INVENTION

The present disclosure relates to ophthalmic formulations comprising carbachol. The formulations disclosed may be useful in treating ophthalmic conditions such as presbyopia.

Presbyopia is typically age-related eye deterioration. Young, properly functioning, eyes have clear, flexible lenses which are able to accommodate to see at near distances, an ability that deteriorates as one ages. Presbyopia normally develops as a person ages, and is associated with a natural progressive loss of accommodation. A presbyopic eye loses the ability to rapidly and easily focus on objects at near distances. Presbyopia progresses over the lifetime of an individual, usually becoming noticeable after the age of 45 years. By the age of 65 years, the crystalline lens has often lost almost all elastic properties and has only limited ability to change shape.

Use of over the counter reading glasses is a very common way of addressing the vision problems associated with presbyopia. Reading glasses allow the eye to focus on near objects and maintain a clear image. This approach is similar to that of treating hyperopia, or farsightedness.

Many presbyopes are also prescribed bi-focal eyeglasses, where one portion of the lens is corrected for distance vision and another portion of the lens is corrected for near vision. When peering down through the bifocals, the individual looks through the portion of the lens corrected for near vision. When viewing distant objects, the individual looks higher, through the portion of the bi-focals corrected for distance vision. Such glasses can be expensive, and depending of the degree of correction required, can leave a user with limited or virtually no peripheral vision. Contact lenses and intra-ocular lenses (IOLs) have also been used to treat presbyopia, for example, by relying on monovision (where one eye is corrected for distance-vision, while the other eye is corrected for near-vision) or bilateral correction with either bi-focal or multi-focal lenses. Laser ablation has also been used to treat presbyopia. All these procedures seek to correct the problem for long term purposes using drastic steps (surgery, laser ablation, etc.) or require wearing corrective lenses. There remains a need for new ways of ameliorating or reducing presbyopia for patients that do not wish to undergo surgery (IOLs, laser ablation, etc.) or use corrective glasses. For people who use corrective lenses, there remains a need to temporarily treat presbyopia without the use of corrective lenses.

BRIEF SUMMARY OF THE INVENTION

Figure 1A:
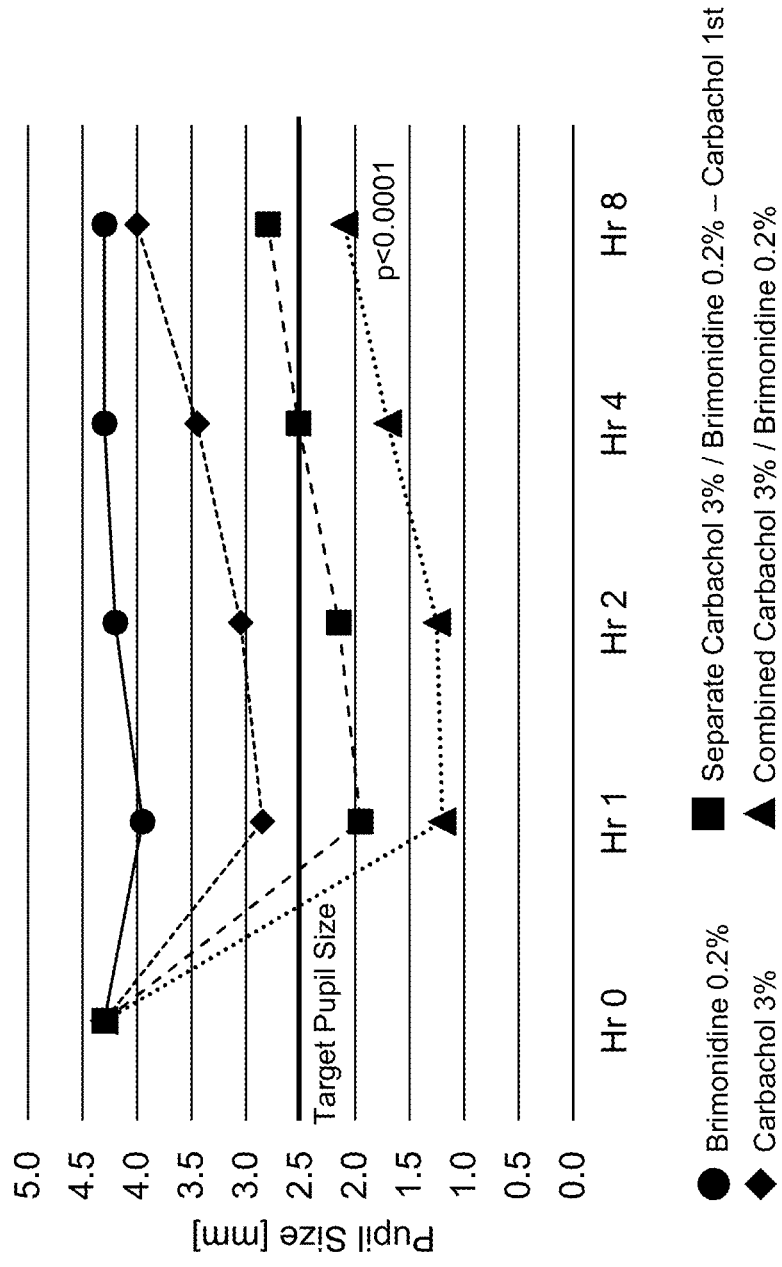
FIGS. 1A and 1B show a comparison of the distribution of mean change in pupil size (mm) and near visual acuity (NVA) in phakic emmetropic presbyopes (n=10) over time (8 hours) between brimonidine/carbachol combination drops, separately administered drops, brimonidine alone, and carbachol alone. The mean change in pupil size is the least in subjects treated with 0.2% brimonidine alone, and the most in subjects treated with the 0.2% brimonidine/3% carbachol combination.

The present disclosure provides ophthalmic formulations comprising carbachol.

In some aspects, the ophthalmic formulation comprises from about 0.75 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agents and from about 0.05 wt % to about 1 wt % of one or more buffers, wherein the pH of the formulation is from about 7 to about 7.6.

An ophthalmic formulation consisting essentially of from about 0.75 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agents, and from about 0.05 wt % to about 1 wt % of one or more buffers, wherein the pH of the formulation is from about 7 to about 7.6.

An ophthalmic formulation consisting of from about 0.75 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agents, and from about 0.05 wt % to about 1 wt % of one or more buffers, wherein the pH of the formulation is from about 7 to about 7.6.

In some aspects, the ophthalmic formulation comprises about 2.75 wt % carbachol, about 0.2 wt % HPMC, from about 0.013 wt % sodium chloride and from about 0.05 wt % to about 1 wt % of one or more buffers, wherein the pH is about 7.4.

In some aspects, the ophthalmic formulation consisting essentially of about 2.75 wt % carbachol, about 0.2 wt % HPMC, from about 0.013 wt % sodium chloride and from about 0.05 wt % to about 1 wt % of one or more buffers, wherein the pH is about 7.4.

In some aspects, the ophthalmic formulation consisting of about 2.75 wt % carbachol, about 0.2 wt % HPMC, from about 0.013 wt % sodium chloride and from about 0.05 wt % to about 1 wt % of one or more buffers, wherein the pH is about 7.4.

In some aspects, the ophthalmic formulation comprises about 2.75 wt % carbachol, about 0.013 wt % sodium chloride and about 0.2 wt % HPMC, wherein the pH is about 7.4.

In some aspects, the ophthalmic formulation comprises from about 0.75 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agents, and from about 0.05 wt % to about 0.1 wt % of one or more buffers, wherein the pH of the formulation is from about 7 to about 7.6.

In some aspects, the ophthalmic formulation comprises about 2.75 wt % carbachol, about 0.2 wt % HPMC, about 0.013 wt % sodium chloride, and from about 0.05 wt % to about 1 wt % of one or more buffers, wherein the pH is about 7.4.

In some aspects, an ophthalmic formulation described herein comprises only one active agent, carbachol, or a pharmaceutically acceptable salt thereof.

In some aspects, an ophthalmic formulation described herein does not contain brimonidine, or a pharmaceutically acceptable salt thereof.

In some aspects, an ophthalmic formulation described herein comprises one or more buffers selected from the group consisting of acetate buffer, borate buffer, borate citrate buffer, carbonate buffer, citrate buffer, lactate buffer, and phosphate buffer.

In some aspects, an ophthalmic formulation described herein comprises one or more buffers that is a phosphate buffer.

In some aspects, the phosphate buffer comprises sodium phosphate monobasic monohydrate and sodium phosphate dibasic heptahydrate.

In some aspects, an ophthalmic formulation described herein comprises one or more viscosity agents selected from the group consisting of hydroxypropylmethyl cellulose (HPMC), hydroxyethyl cellulose, methyl cellulose, carboxymethyl cellulose, and polyvinyl alcohol, and polyvinylpyrrolidone.

In some aspects, an ophthalmic formulation described herein comprises HPMC.

In some aspects, an ophthalmic formulation described herein comprises one or more tonicity agents selected from the group consisting of sodium chloride or potassium chloride, organic compounds such as propylene glycol, mannitol, sorbitol, dextrose, and glycerin.

In some aspects, an ophthalmic formulation described herein comprises sodium chloride.

In some aspects, an ophthalmic formulation described herein comprises from about 0.0025 wt % to about 0.02 wt % benzalkonium chloride.

In some aspects, an ophthalmic formulation described herein comprises from about 0 ppm to about 200 ppm benzalkonium chloride.

In some aspects, an ophthalmic formulation described herein does not contain benzalkonium chloride. In some aspects, an ophthalmic formulation described herein does not contain EDTA.

The present disclosure also provides processes for preparing ophthalmic formulations comprising carbachol.

In some aspects, the disclosure provides a process for manufacturing an ophthalmic formulation comprising from about 0.75 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agents and from about 0.05 wt % to about 1 wt % of one or more buffers, wherein the pH of the formulation is from about 7 to about 7.6, the process comprising adding carbachol, or a pharmaceutically acceptable salt thereof, one or more tonicity agents, and one or more viscosity agents to water and mixing to provide the formulation.

In some aspects, the one or more buffers comprise sodium phosphate monobasic monohydrate and sodium phosphate dibasic heptahydrate.

In some aspects, the one or more viscosity agents is hydroxypropylmethyl cellulose (HPMC).

In some aspects, the one or more tonicity agents is sodium chloride.

In some aspects, the process comprises adding benzalkonium chloride.

In some aspects, the process comprises adding sodium chloride.

In some aspects, the process comprises adding hydrochloric acid.

In some aspects, the process comprises adding sodium hydroxide.

In some aspects, the ophthalmic formulation is aseptically filled into vials.

In some aspects, each vial is filled with from about 0.1 g to about 0.3 g of the ophthalmic formulation.

In some aspects, each vial is filled with from about 2 g to about 2.7 g of the ophthalmic formulation.

The present disclosure also provides methods of ameliorating or reducing presbyopia in a subject comprising administering an ophthalmic formulation described herein.

The present disclosure also provides methods of ameliorating or reducing at least one refractive error of subject with hyperopia, relaxing a ciliary muscle of a subject stimulated by sympathetic innervation to reduce at least one of headache, browache and periorbital pain, preventing a parasympathomimetic induced myopic shift in a patient with presbyopia receiving parasympathomimetic drugs or pharmaceutically acceptable salts thereof, ameliorating or reducing at least one refractive error of a pseudophakic patient selected from the group consisting of myopia, hyperopia, and astigmatism, treating at least one refractive error in a patient that has had ocular surgery, and creating multifocality in a pseudophakic patient, comprising administering an ophthalmic formulation described herein.

DETAILED DESCRIPTION OF THE INVENTION

Definitions

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

In order to further define this disclosure, the following terms and definitions are provided.

The singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "pharmaceutically acceptable" as used herein refers to those compounds, materials, compositions, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "excipient" refers to any substance, not itself a therapeutic agent, which may be used in a composition for delivery of an active therapeutic agent to a subject or combined with an active therapeutic agent (e.g., to create a pharmaceutical composition) to improve its handling or storage properties or to permit or facilitate formation of a dose unit of the composition. The excipient can be an inert substance, an inactive substance, and/or a not medicinally active substance.

The terms "effective amount" or "pharmaceutically effective amount" or "therapeutically effective amount" as used herein refer to the amount or quantity of a drug or pharmaceutically active substance which is sufficient to elicit the required or desired therapeutic response, or in other words, the amount which is sufficient to elicit an appreciable biological response when administered to a patient.

"Administration", or "to administer" means the step of giving (i.e. providing) a pharmaceutical composition to a subject. The pharmaceutical compositions disclosed herein can be "locally administered", that is administered at or in the vicinity of the site at which a therapeutic result or outcome is desired. For example to treat an ocular condition such as corneal pain, topical administration, directly to the eye of a subject, of an ophthalmic formulation can be carried out, and is an example of local administration.

The term "pharmaceutically acceptable salts" is art-recognized, and includes relatively non-toxic, inorganic and organic acid addition salts of compounds and relatively non-toxic, inorganic and organic base addition salts of compounds.

Inorganic acids which may be used to prepare pharmaceutically acceptable salts include, but are not limited to, hydrochloric acid, phosphoric acid, sulfuric acid, hydrobromic acid, hydroiodic acid, phosphorous acid and the like. Organic acids which may be used to prepare pharmaceutically acceptable salts include, without limitation, aliphatic mono- and dicarboxylic acids, such as tartaric acid, oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include, but are not limited to, hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroiodide, hydrofluoride, acetate, propionate, formate, oxalate, tartrate, citrate, lactate, p-toluenesulfonate, methanesulfonate, and maleate. Suitable pharmaceutically acceptable salts may also be formed by reacting the active components with an organic base such as methylamine, ethylamine, ethanolamine, lysine, ornithine and the like. Pharmaceutically acceptable salts include the salts formed between carboxylate or sulfonate groups that may be found on some of the active components and inorganic cations, such as sodium, potassium, ammonium, or calcium, or such organic cations as isopropylammonium, trimethylammonium, tetramethylammonium, and imidazolium. All of these salts may be prepared by conventional means from the active components of the invention by reacting, for example, the appropriate acid or base with the active components of the invention.

The term "unit dosage form" or "unit dose composition" as used herein refers to a quantity of a compound, such as a drop or a droplet, said quantity being such that one or more predetermined units may be provided as a single therapeutic administration.

As used herein, "treat," "treatment", and "treating" refer to the reduction or amelioration of the progression, severity, and/or duration of a given disease resulting from the administration of one or more therapies (including, but not limited to, the administration of an ophthalmic formulation). In certain aspects, the terms refer to the reduction of pain associated with one or more diseases or conditions.

The term "wt %" or "weight/volume" as used herein refers to the ratio between two components with respect to volume. For example, a 5 wt % ethanol in water solution would represent a solution comprising 5 g ethanol for every 100 mL water.

The term "mg/mL" as used herein refers to the ratio between a solute, generally an active pharmaceutical ingredient or excipient, and a solvent, generally but not necessarily water. For example, a 50 mg/mL sodium chloride aqueous solution would represent a solution comprising 50 mg sodium chloride for every 1 mL water.

Ophthalmic Formulations

The present disclosure also provides ophthalmic formulations comprising carbachol.

In some aspects, the ophthalmic formulation comprises from about 0.75 wt % to about 4 wt % carbachol, or a pharmaceutically acceptable salt thereof, from about 0.05 wt % to about 1 wt % of one or more viscosity agents, from about 0.01 wt % to about 0.02 wt % of one or more tonicity agents, and from about 0.05 wt % to about 1 wt % of one or more buffers, wherein the pH of the formulation is from about 7 to about 7.6.

In some aspects, the ophthalmic formulation comprises from about 0.25 wt % to about 0.5 wt %, from about 0.25 wt % to about 0.75 wt %, from about 0.25 wt % to about 1 wt %, from about 0.25 wt % to about 1.25 wt %, from about 0.25 wt % to about 1.5 wt %, from about 0.25 wt % to about 1.75 wt %, from about 0.25 wt % to about 2 wt %, from about 0.25 wt % to about 2.25 wt %, from about 0.25 wt % to about 2.5 wt %, from about 0.25 wt % to about 2.75 wt %, from about 0.25 wt % to about 3 wt %, from about 0.25 wt % to about 3.25 wt %, from about 0.25 wt % to about 3.5 wt %, from about 0.25 wt % to about 3.75 wt %, from about 0.25 wt % to about 4 wt %, from about 0.25 wt % to about 4.25 wt %, from about 0.25 wt % to about 4.5 wt %, from about 0.25 wt % to about 4.75 wt %, from about 0.25 wt % to about 5 wt %, from about 0.5 wt % to about 0.75 wt %, from about 0.5 wt % to about 1 wt %, from about 0.5 wt % to about 1.25 wt %, from about 0.5 wt % to about 1.5 wt %, from about 0.5 wt % to about 1.75 wt %, from about 0.5 wt % to about 2 wt %, from about 0.5 wt % to about 2.25 wt %, from about 0.5 wt % to about 2.5 wt %, from about 0.5 wt % to about 2.75 wt %, from about 0.5 wt % to about 3 wt %, from about 0.5 wt % to about 3.25 wt %, from about 0.5 wt % to about 3.5 wt %, from about 0.5 wt % to about 3.75 wt %, from about 0.5 wt % to about 4 wt %, from about 0.5 wt % to about 4.25 wt %, from about 0.5 wt % to about 4.5 wt %, from about 0.5 wt % to about 4.75 wt %, from about 0.5 wt % to about 5 wt %, from about 0.75 wt % to about 1 wt %, from about 0.75 wt % to about 1.25 wt %, from about 0.75 wt % to about 1.5 wt %, from about 0.75 wt % to about 1.75 wt %, from about 0.75 wt % to about 2 wt %, from about 0.75 wt % to about 2.25 wt %, from about 0.75 wt % to about 2.5 wt %, from about 0.75 wt % to about 2.75 wt %, from about 0.75 wt % to about 3 wt %, from about 0.75 wt % to about 3.25 wt %, from about 0.75 wt % to about 3.5 wt %, from about 0.75 wt % to about 3.75 wt %, from about 0.75 wt % to about 4 wt %, from about 0.75 wt % to about 4.25 wt %, from about 0.75 wt % to about 4.5 wt %, from about 0.75 wt % to about 4.75 wt %, from about 0.75 wt % to about 5 wt %, from about 1 wt % to about 1.25 wt %, from about 1 wt % to about 1.5 wt %, from about 1 wt % to about 1.75 wt %, from about 1 wt % to about 2 wt %, from about 1 wt % to about 2.25 wt %, from about 1 wt % to about 2.5 wt %, from about 1 wt % to about 2.75 wt %, from about 1 wt % to about 3 wt %, from about 1 wt % to about 3.25 wt %, from about 1 wt % to about 3.5 wt %, from about 1 wt % to about 3.75 wt %, from about 1 wt % to about 4 wt %, from about 1 wt % to about 4.25 wt %, from about 1 wt % to about 4.5 wt %, from about 1 wt % to about 4.75 wt %, from about 1 wt % to about 5 wt %, carbachol, from about 1.25 wt % to about 1.5 wt %, from about 1.25 wt % to about 1.75 wt %, from about 1.25 wt % to about 2 wt %, from about 1.25 wt % to about 2.25 wt %, from about 1.25 wt % to about 2.5 wt %, from about 1.25 wt % to about 2.75 wt %, from about 1.25 wt % to about 3 wt %, from about 1.25 wt % to about 3.25 wt %, from about 1.25 wt % to about 3.5 wt %, from about 1.25 wt % to about 3.75 wt %, from about 1.25 wt % to about 4 wt %, from about 1.25 wt % to about 4.25 wt %, from about 1.25 wt % to about 4.5 wt %, from about 1.25 wt % to about 4.75 wt %, from about 1.25 wt % to about 5 wt %, from about 1.5 wt % to about 1.75 wt %, from about 1.5 wt % to about 2 wt %, from about 1.5 wt % to about 2.25 wt %, from about 1.5 wt % to about 2.5 wt %, from about 1.5 wt % to about 2.75 wt %, from about 1.5 wt % to about 3 wt %, from about 1.5 wt % to about 3.25 wt %, from about 1.5 wt % to about 3.5 wt %, from about 1.5 wt % to about 3.75 wt %, from about 1.5 wt % to about 4 wt %, from about 1.5 wt % to about 4.25 wt %, from about 1.5 wt % to about 4.5 wt %, from about 1.5 wt % to about 4.75 wt %, from about 1.5 wt % to about 5 wt %, from about 1.75 wt % to about 2 wt %, from about 1.75 wt % to about 2.25 wt %, from about 1.75 wt % to about 2.5 wt %, from about 1.75 wt % to about 2.75 wt %, from about 1.75 wt % to about 3 wt %, from about 1.75 wt % to about 3.25 wt %, from about 1.75 wt % to about 3.5 wt %, from about 1.75 wt % to about 3.75 wt %, from about 1.75 wt % to about 4 wt %, from about 1.75 wt % to about 4.25 wt %, from about 1.75 wt 00 to about 4.5 wt 00 from about 1.75 wt 00 to about 4.75 wt 00 from about 1.75 wt % to about 5 wt %, from about 2 wt % to about 2.25 wt %, from about 2 wt % to about 2.5 wt %, from about 2 wt % to about 2.75 wt %, from about 2 wt % to about 3 wt %, from about 2 wt % to about 3.25 wt %, from about 2 wt % to about 3.5 wt %, from about 2 wt % to about 3.75 wt %, from about 2 wt % to about 4 wt %, from about 2 wt % to about 4.25 wt %, from about 2 wt % to about 4.5 wt %, from about 2 wt % to about 4.75 wt %, from about 2 wt % to about 5 wt %, from about 2.25 wt % to about 2.5 wt %, from about 2.25 wt % to about 2.75 wt %, from about 2.25 wt % to about 3 wt %, from about 2.25 wt % to about 3.25 wt %, from about 2.25 wt % to about 3.5 wt %, from about 2.25 wt % to about 3.75 wt %, from about 2.25 wt % to about 4 wt %, from about 2.25 wt % to about 4.25 wt %, from about 2.25 wt % to about 4.5 wt %, from about 2.25 wt % to about 4.75 wt %, from about 2.25 wt % to about 5 wt %, from about 2.5 wt % to about 2.75 wt %, from about 2.5 wt % to about 3 wt %, from about 2.5 wt % to about 3.25 wt %, from about 2.5 wt % to about 3.5 wt %, from about 2.5 wt % to about 3.75 wt %, from about 2.5 wt % to about 4 wt %, from about 2.5 wt % to about 4.25 wt %, from about 2.5 wt % to about 4.5 wt %, from about 2.5 wt % to about 4.75 wt %, from about 2.5 wt % to about 5 wt %, from about 2.7 wt % to about 2.8 wt %, from about 2.65 wt % to about 2.85 wt %, from about 2.6 wt % to about 2.9 wt %, from about 2.5 wt % to about 3 wt %, from about 2.75 wt % to about 3 wt %, from about 2.75 wt % to about 3.25 wt %, from about 2.75 wt % to about 3.5 wt %, from about 2.75 wt % to about 3.75 wt %, from about 2.75 wt % to about 4 wt %, from about 2.75 wt % to about 4.25 wt %, from about 2.75 wt % to about 4.5 wt %, from about 2.75 wt % to about 4.75 wt %, from about 2.75 wt % to about 5 wt %, from about 3 wt % to about 3.25 wt %, from about 3 wt % to about 3.5 wt %, from about 3 wt % to about 3.75 wt %, from about 3 wt % to about 4 wt %, from about 3 wt % to about 4.25 wt %, from about 3 wt % to about 4.5 wt %, from about 3 wt % to about 4.75 wt %, from about 3 wt % to about 5 wt %, from about 3.25 wt % to about 3.5 wt %, from about 3.25 wt % to about 3.75 wt %, from about 3.25 wt % to about 4 wt %, from about 3.25 wt % to about 4.25 wt %, from about 3.25 wt % to about 4.5 wt %, from about 3.25 wt % to about 4.75 wt %, from about 3.25 wt % to about 5 wt %, from about 3.5 wt % to about 3.75 wt %, from about 3.5 wt % to about 4 wt %, from about 3.5 wt % to about 4.25 wt %, from about 3.5 wt % to about 4.5 wt %, from about 3.5 wt % to about 4.75 wt %, from about 3.5 wt % to about 5 wt %, from about 3.75 wt % to about 4 wt %, from about 3.75 wt % to about 4.25 wt %, from about 3.75 wt % to about 4.5 wt %, from about 3.75 wt % to about 4.75 wt %, from about 3.75 wt % to about 5 wt %, from about 4 wt % to about 4.25 wt 00 from about 4 wt % to about 4.5 wt %, from about 4 wt % to about 4.75 wt %, from about 4 wt % to about 5 wt %, from about 4.25 wt % to about 4.5 wt %, from about 4.25 wt % to about 4.75 wt %, from about 4.25 wt % to about 5 wt %, from about 4.5 wt % to about 4.75 wt %, from about 4.5 wt % to about 5 wt %, or from about 4.75 wt % to about 5 wt % carbachol, or a pharmaceutically acceptable salt thereof. In some aspects, the ophthalmic formulation comprises from about 1 wt % to about 4 wt % carbachol, or a pharmaceutically acceptable salt thereof.

In some aspects, the ophthalmic formulation comprises about 0.25 wt %, about 0.5 wt %, about 0.75 wt %, about 1 wt %, about 1.25 wt %, about 1.5 wt %, about 1.75 wt %, about 2 wt %, about 2.25 wt %, about 2.5 wt %, about 2.6 wt %, about 2.65 wt %, about 2.7 wt %, about 2.75 wt %, about 2.8 wt %, about 2.85 wt %, about 2.9 wt %, about 3 wt %, about 3.25 wt %, about 3.5 wt %, about 3.75 wt %, about 4 wt %, about 4.25 wt %, about 4.5 wt %, about 4.75 wt %, or about 5 wt % carbachol, or a pharmaceutically acceptable salt thereof. In some aspects, the ophthalmic formulation comprises about 2.75 wt % carbachol, or a pharmaceutically acceptable salt thereof.

In some aspects, the ophthalmic formulation comprises one or more viscosity agents. Non-limiting examples of viscosity agents include hydroxypropyl methylcellulose (HPMC), hydroxyethyl cellulose, hydroxypropyl cellulose, polyvinylpyrrolidone, carboxymethyl cellulose, polyvinyl alcohol, sodium chondroitin sulfate, and sodium hyaluronate. Other acceptable viscosity agents include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), silicon dioxide, polyvinylpyrrolidone (PVP: povidone), Splenda® (dextrose, maltodextrin and sucralose) and combinations thereof.

In some aspects, the ophthalmic formulation comprises hydroxypropylmethyl cellulose or carboxymethyl cellulose.

In some aspects, the ophthalmic formulation comprises from about 0 wt % to about 0.1 wt %, from about 0 wt % to about 0.25 wt %, from about 0 wt % to about 0.5 wt %, from about 0 wt % to about 0.75 wt %, from about 0 wt % to about 1 wt %, from about 0.1 wt % to about 0.25 wt %, from about 0.1 wt % to about 0.5 wt %, from about 0.1 wt % to about 0.75 wt %, from about 0.1 wt % to about 1 wt %, from about 0.25 wt % to about 0.5 wt %, from about 0.25 wt % to about 0.75 wt %, from about 0.25 wt % to about 1 wt %, from about 0.5 wt % to about 0.75 wt %, from about 0.5 wt % to about 1 wt %, or from about 0.75 wt % to about 1 wt % of one or more viscosity agents. In some aspects, the ophthalmic formulation comprises from about 0 wt % to about 1 wt % of one or more viscosity agents.

In some aspects, the ophthalmic formulation comprises about 0 wt %, about 0.1 wt %, about 0.15 wt %, about 0.2 wt %, about 0.25 wt %, about 0.5 wt %, about 0.75 wt %, or about 1 wt % of one or more viscosity agents. In some aspects, the ophthalmic formulation comprises about 0.2 wt % of one or more viscosity agents.

In some aspects, the viscosity of the ophthalmic formulation is from about 1 cPs to about 5 cPs, from about 1 cPs to about 10 cPs, from about 1 cPs to about 15 cPs, from about 1 cPs to about 20 cPs, from about 1 cPs to about 30 cPs, from about 1 cPs to about 40 cPs, from about 1 cPs to about 50 cPs, from about 1 cPs to about 60 cPs, from about 1 cPs to about 80 cPs, from about 1 cPs to about 100 cPs, from about 1 cPs to about 125 cPs, from about 1 cPs to about 150 cPs, from about 1 cPs to about 175 cPs, from about 1 cPs to about 200 cPs, from about 1 cPs to about 400 cPs, from about 5 cPs to about 10 cPs, from about 5 cPs to about 15 cPs, from about 5 cPs to about 20 cPs, from about 5 cPs to about 30 cPs, from about 5 cPs to about 40 cPs, from about 5 cPs to about 50 cPs, from about 5 cPs to about 60 cPs, from about 5 cPs to about 80 cPs, from about 5 cPs to about 100 cPs, from about 5 cPs to about 125 cPs, from about 5 cPs to about 150 cPs, from about 5 cPs to about 175 cPs, from about 5 cPs to about 200 cPs, from about 5 cPs to about 400 cPs, from about 10 cPs to about 15 cPs, from about 10 cPs to about 20 cPs, from about 10 cPs to about 30 cPs, from about 10 cPs to about 40 cPs, from about 10 cPs to about 50 cPs, from about 10 cPs to about 60 cPs, from about 10 cPs to about 80 cPs, from about 10 cPs to about 100 cPs, from about 10 cPs to about 125 cPs, from about 10 cPs to about 150 cPs, from about 10 cPs to about 175 cPs, from about 10 cPs to about 200 cPs, from about 10 cPs to about 400 cPs, from about 15 cPs to about 20 cPs, from about 15 cPs to about 30 cPs, from about 15 cPs to about 40 cPs, from about 15 cPs to about 50 cPs, from about 15 cPs to about 60 cPs, from about 15 cPs to about 80 cPs, from about 15 cPs to about 100 cPs, from about 15 cPs to about 125 cPs, from about 15 cPs to about 150 cPs, from about 15 cPs to about 175 cPs, from about 15 cPs to about 200 cPs, from about 15 cPs to about 400 cPs, from about 20 cPs to about 30 cPs, from about 20 cPs to about 40 cPs, from about 20 cPs to about 50 cPs, from about 20 cPs to about 60 cPs, from about 20 cPs to about 80 cPs, from about 20 cPs to about 100 cPs, from about 20 cPs to about 125 cPs, from about 20 cPs to about 150 cPs, from about 20 cPs to about 175 cPs, from about 20 cPs to about 200 cPs, from about 20 cPs to about 400 cPs, from about 30 cPs to about 40 cPs, from about 30 cPs to about 50 cPs, from about 30 cPs to about 60 cPs, from about 30 cPs to about 80 cPs, from about 30 cPs to about 100 cPs, from about 30 cPs to about 125 cPs, from about 30 cPs to about 150 cPs, from about 30 cPs to about 175 cPs, from about 30 cPs to about 200 cPs, from about 30 cPs to about 400 cPs, from about 40 cPs to about 50 cPs, from about 40 cPs to about 60 cPs, from about 40 cPs to about 80 cPs, from about 40 cPs to about 100 cPs, from about 40 cPs to about 125 cPs, from about 40 cPs to about 150 cPs, from about 40 cPs to about 175 cPs, from about 40 cPs to about 200 cPs, from about 40 cPs to about 400 cPs, from about 50 cPs to about 60 cPs, from about 50 cPs to about 80 cPs, from about 50 cPs to about 100 cPs, from about 50 cPs to about 125 cPs, from about 50 cPs to about 150 cPs, from about 50 cPs to about 175 cPs, from about 50 cPs to about 200 cPs, from about 50 cPs to about 400 cPs, from about 60 cPs to about 80 cPs, from about 60 cPs to about 100 cPs, from about 60 cPs to about 125 cPs, from about 60 cPs to about 150 cPs, from about 60 cPs to about 175 cPs, from about 60 cPs to about 200 cPs, from about 60 cPs to about 400 cPs, from about 80 cPs to about 100 cPs, from about 80 cPs to about 125 cPs, from about 80 cPs to about 150 cPs, from about 80 cPs to about 175 cPs, from about 80 cPs to about 200 cPs, from about 80 cPs to about 400 cPs, from about 100 cPs to about 125 cPs, from about 100 cPs to about 150 cPs, from about 100 cPs to about 175 cPs, from about 100 cPs to about 200 cPs, from about 100 cPs to about 400 cPs, from about 125 cPs to about 150 cPs, from about 125 cPs to about 175 cPs, from about 125 cPs to about 200 cPs, from about 125 cPs to about 400 cPs, from about 150 cPs to about 175 cPs, from about 150 cPs to about 200 cPs, from about 150 cPs to about 400 cPs, from about 175 cPs to about 200 cPs, from about 175 cPs to about 400 cPs, or from about 200 cPs to about 400 cPs. In some aspects, the viscosity of the ophthalmic formulation is from about 10 cPs to about 30 cPs.

In some aspects, the ophthalmic formulation has a viscosity of about 1 cPs, about 5 cPs, about 10 cPs, about 15 cPs, about 20 cPs, about 30 cPs, about 40 cPs, about 50 cPs, about 60 cPs, about 80 cPs, about 100 cPs, about 125 cPs, about 150 cPs, about 175 cPs, about 200 cPs, or about 400 cPs. In some aspects, the ophthalmic formulation has a viscosity of about 30 cPs.

In some aspects, the ophthalmic formulation comprises one or more buffers. Non-limiting examples of buffers include acetate buffer, borate buffer, borate citrate buffer, citrate buffer, lactate buffer, phosphate buffer, succinate buffer, borate-polyol complex buffer, carbonate buffer, an organic buffer, an amino acid buffer, and combinations thereof. In some aspects, the ophthalmic formulation comprises one or more buffers that is a phosphate buffer.

In some aspects, the phosphate buffer comprises phosphoric acid; alkali metal phosphates such as disodium hydrogen phosphate, sodium phosphate monobasic monohydrate, sodium dihydrogen phosphate, sodium phosphate dibasic heptahydrate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; ammonium phosphates such as diammonium hydrogen phosphate and ammonium dihydrogen phosphate; or a combination thereof. In some aspects, the phosphate buffer comprises one or more anhydrides. In some aspects, the phosphate buffer comprises one or more hydrates.

Organic buffers include, but are not limited to, Good's Buffer, such as for example 2-(N-morpholino)ethanesulfonic acid (MES), N-(2-Acetamido)iminodiacetic acid, N-(Carbamoylmethyl)iminodiacetic acid (ADA), piperazine-N,N'-bis(2-ethanesulfonic acid (PIPES), N-(2-acetamido)-2-aminoethanesulfonic acid (ACES), β-Hydroxy-4-morpholinepropanesulfonic acid, 3-Morpholino-2-hydroxypropanesulfonic acid (MOPSO), cholamine chloride, 3-(N-morpholino)propansulfonic acid (MOPS), N,N-bis(2-hydroxyethyl)-2-aminoethanesulfonic acid (BES), 2-[(2-Hydroxy-1,1-bis(hydroxymethyl)ethyl)amino] ethanesulfonic acid (TES), 4-(2-hydroxyethyl)-1-piperazineethanesulfonic acid (HEPES), 3-(N,N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), piperazine-1,4,-bis (2-hydroxypropanesulphonic acid) (POPSO), 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, glycinamide, bicine or N-tris(hydroxymethyl) methyl-3-aminopropanesulfonic acid sodium (TAPS); glycine; diethanolamine (DEA); and combinations thereof.

Amino acid buffers include, but are not limited to, taurine, aspartic acid and its salts (e.g., potassium salts, etc), ε-aminocaproic acid, and combinations thereof.

In some aspects, the ophthalmic formulation comprises from about 0.05 wt % to about 0.1 wt %, from about 0.05 wt % to about 0.25 wt %, from about 0.05 wt % to about 0.5 wt %, from about 0.05 wt % to about 0.75 wt %, from about 0.1 wt % to about 0.25 wt %, from about 0.1 wt % to about 0.5 wt %, from about 0.1 wt % to about 0.75 wt %, from about 0.1 wt % to about 1 wt %, from about 0.25 wt % to about 0.5 wt %, from about 0.25 wt % to about 0.75 wt %, from about 0.25 wt % to about 1 wt %, from about 0.3 wt % to about 0.4 wt %, from about 0.3 wt % to about 0.35 wt %, from about 0.5 wt % to about 0.75 wt %, from about 0.5 wt % to about 1 wt %, or from about 0.75 wt % to about 1 wt % of one or more buffers. In some aspects, the ophthalmic formulation comprises from about 0.05 wt % to about 1 wt % of one or more buffers.

In some aspects, the ophthalmic formulation comprises about 0.05 wt %, about 0.1 wt %, about 0.15 wt %, about 0.2 wt %, about 0.25 wt %, about 0.4 wt %, about 0.45 wt 0 about 0.5 wt %, about 0.55 wt %, about 0.6 wt %, about 0.65 wt %, about 0.7 wt %, about 0.75 wt %, about 0.8 wt %, about 0.85 wt %, about 0.9 wt %, about 0.95 wt %, or about 1 wt % of one or more buffers. In some aspects, the ophthalmic formulation comprises about 0.3 wt % of one or more buffers. In some aspects, the ophthalmic formulation comprises about 0.35 wt % of one or more buffers.

In some aspects, the ophthalmic formulation has a pH of from about 6 to about 6.5, from about 6 to about 7, from about 6 to about 7.2, from about 6 to about 7.4, from about 6 to about 7.6, from about 6 to about 7.8, from about 6 to about 8, from about 6.5 to about 7, from about 6.5 to about 7.2, from about 6.5 to about 7.4, from about 6.5 to about 7.6, from about 6.5 to about 7.8, from about 6.5 to about 8, from about 7 to about 7.2, from about 7 to about 7.4, from about 7 to about 7.8, from about 7 to about 8, from about 7.2 to about 7.4, from about 7.2 to about 7.6, from about 7.2 to about 7.8, from about 7.2 to about 8, from about 7.4 to about 7.6, from about 7.4 to about 7.8, from about 7.4 to about 8, or from about 7.6 to about 7.8. In some aspects, the ophthalmic formulation has a pH of from about 7 to about 7.6.

In some aspects, the ophthalmic formulation has a pH of about 6, about 6.5, about 7, about 7.2, about 7.6, or about 8. In some aspects, the ophthalmic formulation has a pH of about 7.4.

In some aspects, the pH of the ophthalmic formulation is adjusted by a strong acid or base. Examples of strong acids and strong bases are well known in the art and include, without limitation, NaOH, KOH, HCl, and $H_2SO_4$. In some aspects, the strong acid or base is HCl or NaOH.

In some aspects, the ophthalmic formulation comprises one or more tonicity agents. Non-limiting examples of tonicity agents include sodium chloride or potassium chloride, organic compounds such as propylene glycol, mannitol, sorbitol, dextrose, and glycerin. In some aspects, the ophthalmic formulation comprises one or more tonicity agents that is sodium chloride.

In some aspects, the ophthalmic formulation comprises from about 0.005 wt % to about 0.01 wt %, from about 0.005 wt % to about 0.02 wt %, from about 0.005 wt % to about 0.03 wt %, from about 0.005 wt % to about 0.04 wt %, from about 0.005 wt % to about 0.05 wt %, from about 0.01 wt % to about 0.02 wt %, from about 0.01 wt % to about 0.03 wt %, from about 0.01 wt % to about 0.04 wt %, from about 0.01 wt % to about 0.05 wt % tonicity agent. In some aspects, the ophthalmic formulation comprises from about 0.01 wt % to about 0.02 wt % tonicity agent. In some aspects, the ophthalmic formulation comprises about 0.013 wt % tonicity agent.

In some aspects, the ophthalmic formulation comprises a preservative. Non-limiting examples of preservatives include benzalkonium chloride, stabilized oxychloro complexes (Purite®), phenylmercuric acetate, chlorobutanol, benzyl alcohol, parabens, EDTA and thimerosal.

In some aspects, the ophthalmic formulation does not contain a preservative.

In some aspects, the ophthalmic formulation does not contain etheylenediaminetetraacetic acid (EDTA).

In some aspects, the ophthalmic formulation comprises a permeation enhancer. Non-limiting examples of permeation enhancers include benzalkonium chloride, laurocapram (azone), bile acids and their alkali metal salts, including chenodeoxycholoc acid, cholic acid, taurocholic acid, taurodeoxycholic acid, tauroursodeoxycholic acid or ursodeoxycholic acid, glycocholate, n-dodecyl-β-D-maltoside, sucrose dodecanoate, octyl maltoside, decyl maltoside, tridecyl maltoside, tetradecyl maltoside, hexamethylene lauramide, hexamethylene octanamide, glycerol monolaurate, PGML (polyethylene glycol monolaurate), dimethyl sulfoxide, methylsulfonylmethane, sodium fusidate, saponins or any combination thereof. In some aspects, the ophthalmic formulation comprises benzalkonium chloride.

In some aspects, the ophthalmic formulation comprises from about 0.0025 wt % to about 0.005 wt %, from about 0.0025 wt % to about 0.0075 wt %, from about 0.0025 wt % to about 0.01 wt % from about 0.0025 wt % to about 0.0125 wt %, from about 0.0025 wt % to about 0.02 wt % from about 0.005 wt % to about 0.0075 wt % from about 0.005 wt % to about 0.01 wt % from about 0.005 wt % to about 0.0125 wt % from about 0.005 wt % to about 0.02 wt % from about 0.0075 wt % to about 0.01 wt % from about 0.0075 wt % to about 0.02 wt % from about 0.01 wt % to about 0.0125 wt % from about 0.01 wt % to about 0.02 wt %, or from about 0.0125 wt % to about 0.02 wt % permeation enhancer. In some aspects, the ophthalmic formulation comprises from about 0.0075 wt % to about 0.0125 wt % permeation enhancer.

In some aspects, the ophthalmic formulation comprises about 0.0025 wt %, about 0.005 wt %, about 0.0075 wt %, about 0.0110 wt %, about 0.0115 wt %, about 0.0125 wt %, or about 0.02 wt % permeation enhancer. In some aspects, the ophthalmic formulation comprises about 0.01 wt % permeation enhancer.

In some aspects, the ophthalmic formulation comprises from about 0.0025 wt % to about 0.005 wt %, from about 0.0025 wt % to about 0.0075 wt %, from about 0.0025 wt % to about 0.01 wt % from about 0.0025 wt % to about 0.0125 wt %, from about 0.0025 wt % to about 0.02 wt % from about 0.005 wt % to about 0.0075 wt % from about 0.005 wt % to about 0.01 wt % from about 0.005 wt % to about 0.0125 wt % from about 0.005 wt % to about 0.02 wt % from about 0.0075 wt % to about 0.01 wt % from about 0.0075 wt % to about 0.02 wt % from about 0.01 wt % to about 0.0125 wt % from about 0.01 wt % to about 0.02 wt %, or from about 0.0125 wt % to about 0.02 wt % benzalkonium chloride. In some aspects, the ophthalmic formulation comprises from about 0.0075 wt % to about 0.0125 wt % benzalkonium chloride.

In some aspects, the ophthalmic formulation comprises from about 0 ppm to about 25 ppm, from about 0 ppm to about 50 ppm, from about 0 ppm to about 75 ppm, from about 0 ppm to about 100 ppm, from about 0 ppm to about 125 ppm, from about 0 ppm to about 150, from about 0 ppm to about 175 ppm, from about 0 ppm to about 200 ppm benzalkonium chloride. In some aspects, the ophthalmic formulation comprises from about 0 ppm to about 200 ppm benzalkonium chloride.

In some aspects, the ophthalmic formulation comprises about 0.0025 wt %, about 0.005 wt %, about 0.0075 wt %, about 0.0110 wt %, about 0.0115 wt %, about 0.0125 wt 0 or about 0.02 wt % benzalkonium chloride. In some aspects, the ophthalmic formulation comprises about 0.01 wt % benzalkonium chloride.

In some aspects, the ophthalmic formulation does not contain a permeation enhancer.

In some aspects, the ophthalmic formulation does not contain benzalkonium chloride.

In some aspects, the ophthalmic formulation comprises one or more stabilizers. Stabilizers include, but are not limited to, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some aspects, amide analogues of stabilizers are also used. In some aspects, the chosen stabilizer changes the hydrophobicity of the formulation, improves the mixing of various components in the formulation, controls the moisture level in the formula, or controls the mobility of the phase.

In some aspects, the ophthalmic formulation comprises one or more stabilizers in sufficient amounts to inhibit the degradation of the active agents. Examples of such stabilizing agents, include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

In some aspects, the ophthalmic formulation does not contain etheylenediaminetetraacetic acid (EDTA).

In some aspects, the solubility of the components of the ophthalmic formulation may be enhanced by a surfactant or other appropriate co-solvent in the composition. Such co-solvents include polysorbate 20, 60, and 80, Pluronic F68, F-84 and P-103, cyclodextrin, or other agents known to those skilled in the art. In some aspects, the concentration of the co-solvent is from 0.01 wt % to about 2 wt %.

In some aspects, the ophthalmic formulation comprises one or more polyols. As used herein, the term "polyol" includes any compound having at least one hydroxyl group on each of two adjacent carbon atoms that are not in trans configuration relative to each other. The polyol can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. It is contemplated that the polyol may be comprised of two or more different polyols.

In some aspects, the ophthalmic formulation comprises one or moer anti-aggregation additives. Anti-aggregation additives enhance stability of the ophthalmic formulation by reducing the rate of protein aggregation. Anti-aggregation additives include, but are not limited to, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

In some aspects, the ophthalmic formulation comprises one or more antioxidants. Antioxidants include, but are not limited to, ascorbic acid, methionine, sodium thiosulfate, sodium metabisulfite, and combinations thereof. Metal chelating agents, thiol-containing compounds, and other general stabilizing agents may be acceptable antioxidants.

In some aspects, the ophthalmic formulation comprises one or more osmolality agents. Osmolality agents include, but are not limited to, salts, particularly sodium chloride or potassium chloride, organic compounds such as propylene glycol, mannitol, sorbitol, dextrose, and glycerin.

In some aspects, the ophthalmic formulation has an osmolality of from about 260 to about 365 mOsm/kg. In some aspects, the ophthalmic formulation has an osmolality of from about 285 mOsm/kg to about 295 mOsm/kg, from about 285 mOsm/kg to about 305 mOsm/kg, from about 285 mOsm/kg to about 315 mOsm/kg, from about 285 mOsm/kg to about 325 mOsm/kg, from about 285 mOsm/kg to about 335 mOsm/kg, from about 285 mOsm/kg to about 345 mOsm/kg, from about 285 mOsm/kg to about 355 mOsm/kg, from about 285 mOsm/kg to about 365 mOsm/kg, from about 295 mOsm/kg to about 305 mOsm/kg, from about 295 mOsm/kg to about 315 mOsm/kg, from about 295 mOsm/kg to about 325 mOsm/kg, from about 295 mOsm/kg to about 335 mOsm/kg, from about 295 mOsm/kg to about 345 mOsm/kg, from about 295 mOsm/kg to about 355 mOsm/kg, from about 295 mOsm/kg to about 365 mOsm/kg, from about 305 mOsm/kg to about 315 mOsm/kg, from about 305 mOsm/kg to about 325 mOsm/kg, from about 305 mOsm/kg to about 335 mOsm/kg, from about 305 mOsm/kg to about 345 mOsm/kg, from about 305 mOsm/kg to about 355 mOsm/kg, from about 305 mOsm/kg to about 365 mOsm/kg, from about 315 mOsm/kg to about 325 mOsm/kg, from about 315 mOsm/kg to about 335 mOsm/kg, from about 315 mOsm/kg to about 345 mOsm/kg, from about 315 mOsm/kg to about 355 mOsm/kg, from about 315 mOsm/kg to about 365 mOsm/kg, from about 325 mOsm/kg to about 335 mOsm/kg, from about 325 mOsm/kg to about 345 mOsm/kg, from about 325 mOsm/kg to about 355 mOsm/kg, from about 325 mOsm/kg to about 365 mOsm/kg, from about 335 mOsm/kg to about 345 mOsm/kg, from about 335 mOsm/kg to about 355 mOsm/kg, from about 335 mOsm/kg to about 365 mOsm/kg, from about 345 mOsm/kg to about 355 mOsm/kg, from about 345 mOsm/kg to about 365 mOsm/kg, from about 355 mOsm/kg to about 365 mOsm/kg, from about 260 mOsm/kg to about 265 mOsm/kg, from about 260 mOsm/kg to about 275 mOsm/kg, from about 260 mOsm/kg to about 285 mOsm/kg, from about 260 mOsm/kg to about 295 mOsm/kg, from about 260 mOsm/kg to about 305 mOsm/kg, from about 260 mOsm/kg to about 315 mOsm/kg, from about 260 mOsm/kg to about 325 mOsm/kg, from about 260 mOsm/kg to about 335 mOsm/kg, from about 260 mOsm/kg to about 345 mOsm/kg, from about 260 mOsm/kg to about 355 mOsm/kg, from about 260 mOsm/kg to about 365 mOsm/kg, from about 265 mOsm/kg to about 275 mOsm/kg, from about 265 mOsm/kg to about 285 mOsm/kg, from about 265 mOsm/kg to about 295 mOsm/kg, from about 265 mOsm/kg to about 305 mOsm/kg, from about 265 mOsm/kg to about 315 mOsm/kg, from about 265 mOsm/kg to about 325 mOsm/kg, from about 265 mOsm/kg to about 335 mOsm/kg, from about 265 mOsm/kg to about 345 mOsm/kg, from about 265 mOsm/kg to about 355 mOsm/kg, from about 265 mOsm/kg to about 365 mOsm/kg, from about 275 mOsm/kg to about 285 mOsm/kg, from about 275 mOsm/kg to about 295 mOsm/kg, from about 275 mOsm/kg to about 305 mOsm/kg, from about 275 mOsm/kg to about 315 mOsm/kg, from about 275 mOsm/kg to about 325 mOsm/kg, from about 275 mOsm/kg to about 335 mOsm/kg, from about 275 mOsm/kg to about 345 mOsm/kg, from about 275 mOsm/kg to about 355 mOsm/kg, from about 275 mOsm/kg to about 365 mOsm/kg.

In some aspects, the ophthalmic formulation has an osmolality of about 260 mOsm/kg, about 265 mOsm/kg, about 275 mOsm/kg, about 285 mOsm/kg, about 295 mOsm/kg, about 305 mOsm/kg, about 315 mOsm/kg, about 325 mOsm/kg, about 335 mOsm/kg, about 345 mOsm/kg, about 355 mOsm/kg, about 365 mOsm/kg, about 370 mOsm/kg, or about 375 mOsm/kg.

In some aspects, the ophthalmic formulation is isotonic. In some aspects, the ophthalmic formulation is hypotonic. In some aspects, the ophthalmic formulation is hypertonic.

In some aspects, the ophthalmic formulation can include a variety of additional ingredients. Such ingredients include, without limitation, additional therapeutic agents, additional or alternative antimicrobial agents, suspension agents, surfactants, additional or alternative tonicity agents, additional or alternative buffering agents, anti-oxidants, additional or alternative viscosity-modifying agents, chelating agents, or any combinations thereof.

Methods of Treatment

The present disclosure provides methods of treating ocular conditions in a subject in need thereof, comprising administering a topical ophthalmic composition comprising carbachol. As used herein, the term "ocular condition" may refer to any condition, disease, or impairment, which affects or involves the eye or one of the parts or regions of the eye, and includes optical issues causing refractive errors in the eye. Ocular conditions include, but are not limited to presbyopia, myopia, progressive myopia, pathologic myopia, amblyopia, cycloplegia, mydriasis, allergic conjunctivitis, conjunctival hyperemia, red eye, glaucoma, ocular hypertension, night vision symptoms post refractive surgery (e.g., glare, halos or starbursts around lights), accommodative esotropia, glaucoma, ocular hypertension, accommodative insufficiency, hyperopia, anisocoria, astigmatism, amblyopia, Adie's tonic pupil, or other causes of parasympathetic denervation, complications arising after refractive surgery, such as decentered ablations following LASTK or PRK, LASTK undercorrections, LASIK overcorrections, corneal scars, hazing, and refractive errors. In some aspects, the ocular condition is presbyopia.

"Presbyopia" is farsightedness often caused by loss of elasticity of the lens of the eye, occurring typically m middle and old age. Presbyopia is a condition associated with the aging of the eye that results in progressively worsening ability to focus clearly (particularly at close distance). Symptoms include difficulty reading small print, having to hold reading material farther away, headaches, and eyestrain. Most people begin to notice the effects of presbyopia sometime after age 40, when they start having trouble seeing small print clearly—including text messages on their phone. Application of cholinergic agonists (miotic agents) in these subjects is beneficial as the miosis resulting from sphincter muscle contraction creates a "pin-hole effect" that may potentially improve the near and intermediate vision by increasing the depth of field. These cholinergic agonists can thus be used for the treatment of presbyopia, although most effective dosing frequency and dose concentrations have not been defined.

A pinhole camera cuts down on the amount of light going in. Since the more light that is let in requires more focus, the user hardly needs to focus with pinhole cameras. Using a pinhole removes the optical periphery. The treatment methods and compositions described herein use drugs to get the pinhole effect, thus increasing depth of focus dramatically. There are two types of muscles in the eyes: constrictor muscles and dilator muscles. By acting on both of these types of muscles, the unique combination of drugs described herein are able to accomplish a pinhole effect, correcting refractive errors.

A pharmacologic pinhole effect may be induced in at least the non-dominant eyes of any patients with refractive errors. In some aspects, the treatment may be administered in both eyes. In some aspects, the treatment is only administered in the non-dominant eye of emmetropic presbyopes and myopic presbyopes and in both eyes of hyperopic presbyopes and hyperopes. For pure myopes, the pinhole effect may be induced in either the non-dominant eye or both eyes of the myopes.

More specifically, administration of carbachol formulations of the present invention causes the pupil to become small (constriction), In one embodiment, for some of the refractive errors including, but not limited to, presbyopia, the formulations are placed in only one eye, to decrease the likelihood of dimness from the treatment. In another embodiment, for the treatment of presbyopia, the formulation is placed in both eyes in order to optimize the corrective effect of the near-sightedness. For other refractive errors including, but not limited to, hyperopia, the drops are preferably placed in both eyes during treatment but may alternatively be placed only in a single eye. In patients with myopic vision, pseudophakes, or astigmatism, the formulations may be placed in a single eye or in both eyes.

For some refractive errors, it may also be beneficial to administer the pharmaceutical preparations described herein to only a single eye of a patient. In some aspects, blurring of distance vision (a result of accommodative focus) and dimness of vision (a result of pupil constriction) may occur when the compositions are administered to both eyes of a patient. When applied to only a single eye, the benefits of improvement in presbyopia may be obtained with diminished or complete relief of blurring and dimness. It was originally believed that a patient's brain compensates between the treated and untreated eyes thereby reducing the undesired effects. Therefore, the combination of a constricted pupil with its increased depth of field in the treated eye and normal distance vision and brightness in the untreated eye may cause the brain to ignore any monocular blur at distance or near vision when only one eye was treated. However, it was surprisingly shown when the pharmaceutical preparation is applied to both eyes, distance visual acuity is preserved, even though administration of parasympathomimetic drugs, or pharmaceutically acceptable salts thereof, such as pilocarpine and carbachol alone can cause a myopic shift, inducing near sightedness at the expense of distance vision while providing increased depth of focus.

Presbyopia may be diagnosed using one or more types of ocular examination procedures, where such examinations may include testing of one or more of visual acuity, e.g., by use of a Snellen chart, Jaeger chart, Rosenbaum chart or ETDRS Near Chart, refraction, binocular vision and accommodation, plus lens to clear near vision, balanced range of accommodation, amplitude of accommodation, crossed cylinder test, accommodative convergence/accommodation, heterophoria and vergence, and vertical imbalance.

The present disclosure also provides methods of ameliorating or reducing presbyopia in a subject comprising administering an ophthalmic formulation described herein. In some aspects, the ophthalmic formulation comprises about 2.75 wt % carbachol, about 0.2 wt % HPMC, about 0.013 wt % sodium chloride, and from about 0.05 wt % to about 1 wt % of one or more buffers, wherein the pH is about 7.4

When used in the treatment of presbyopia, the methods described herein may result in the improvement of one or more characteristics of presbyopia. In some aspects, administration to a subject of an ophthalmic formulation described herein may result in a reduction in pupil diameter as compared with reduction in pupil diameter observed prior to administration of the ophthalmic formulation. The magnitude of the reduction may vary. In some aspects, the reduction is from about 0.25 mm to about 10 mm, from about 1 mm to about 9 mm, or from about 2 mm to about 8 mm. In some aspects, the reduction is from about 0.25 mm to about 3.0 mm, from about 0.5 mm to about 1.5 mm, or from about 0.5 mm to about 1.0 mm. In some aspects, the methods may result in an improvement in uncorrected near visual acuity or other measures of visual function including uncorrected intermediate or distance vision, contrast sensitivity or depth of focus, amongst other measures. Where visual acuity is measured using a chart, such as a Jaeger or Rosenbaum near card, Snellen card or ETDRS Near Chart, the methods described herein may result in an improvement of one or more lines on the chart, such as 1 to 8 lines or 2 to 6 lines. In some aspects, the methods described herein may result in an improvemet of at least two lines on the chart. In other aspects, the methods described herein may result in an improvemet of at least three lines on the chart. In some aspects, the magnitude of improvement with respect to a letter that can be read at about 20 feet is about 5 feet or more, about 10 feet or more, about 15 feet or more. In some aspects, the magnitude improvement with respect to a letter that can be read at about 20 feet is from about 5 feet to about 60 feet, from about 5 feet to about 30 feet, or from about 10 feet to about 25 feet. In some aspects, visual acuity improves from about 20/40 to about 20/25 or from about 20/40 to about 20/20.

In some aspects, the amelioration or reduction of presbyopia is effective for at least 8 hours. In some aspects, the amelioration or reduction of presbyopia is effective for at least 0.5 hours, at least 1 hour, at least 1.5 hours, at least 2 hours, at least 2.5 hours, at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, at least 8.5 hours, at least 9 hours, at least 9.5 hours, at least 10 hours, at least 12 hours, at least 16 hours, at least 20 hours, or at least 24 hours. In one aspect, the amelioration or reduction of presbyopia is effective for at least 4 hours. In another aspect, amelioration or reduction of presbyopia is effective for at least 6 hours.

In some aspects, administration of the ophthalmic formulation reduces periorbital pain in the subject.

The present disclosure also provides methods of ameliorating or reducing at least one refractive error of subject with hyperopia, relaxing a ciliary muscle of a subject stimulated by sympathetic innervation to reduce at least one of headache, browache and periorbital pain, preventing a parasympathomimetic induced myopic shift in a patient with presbyopia receiving parasympathomimetic drugs or pharmaceutically acceptable salts thereof, ameliorating or reducing at least one refractive error of a pseudophakic patient selected from the group consisting of myopia, hyperopia, and astigmatism, treating at least one refractive error in a patient that has had ocular surgery, and creating multifocality in a pseudophakic patient, comprising administering an ophthalmic formulation described herein. In some aspects, the ophthalmic formulation comprises about 2.75 wt % carbachol, about 0.2 wt % HPMC, about 0.013 wt % sodium chloride, and from about 0.05 wt % to about 1 wt % of one or more buffers, wherein the pH is about 7.4.

In some aspects, administering the ophthalmic formulation to a subject with hyperopia results in vision improvement of at least 20% relative to no treatment. In some aspects, administering the ophthalmic formulation to a subject with hyperopia results in vision improvement of at least 5%, at least 10%, at least 15%, at least 25%, at least 30%, at least 35%, at least 40%, at least 45%, at least 50%, at least 60%, at least 70%, at least 80%, at least 90%, or 100% relative to no treatment.

In some aspects, administration of the ophthalmic formulation results in an increase in the depth of focus in the vision of the subject.

In some aspects, administration of the ophthalmic formulation preserves visual acuity in the vision of the subject.

The ophthalmic preparation may be administered to a subject suffering from myopia, hyperopia, astigmatism, presbyopia or other optical errors as often as needed to cause miosis sufficient to temporarily treat, ameliorate, or reduce these optical errors as well as temporarily create multifocality. These refractive errors all benefit from these drugs to a clinically and practically usable degree which enable patients who needed glasses full time to totally do without them. Thus, the present disclosure further provides methods for temporarily treating, ameliorating, or reducing these optical errors by inducing miosis as well as temporarily creating multifocality.

"Optical errors", or "refractive errors", as defined herein, also known as ammetropia (vision abnormalities), are vision defects or optical imperfections that prevent the eye from properly focusing light, causing blurred vision. The primary refractive errors are myopia (nearsightedness), hyperopia (farsightedness, blurred vision), presbyopia (when the lens in the eye loses flexibility), pseudophakia (a near vision defect created by the implantation of an artificial intraocular lens) and astigmatism (including regular astigmatism, irregular astigmatism and high degrees of regular astigmatism). Some refractive errors occur after cataract surgery or laser surgery.

The terms "ameliorate, ameliorating, and amelioration," as used herein, are intended to refer to a decrease in the severity of the refractive error. The amelioration may be complete, e.g., the total absence of one or more refractive errors. The amelioration may also be partial, such that the amount of the refractive error is less than that which would have been present without the treatment. For example, the extent of the refractive errors using the methods of the present invention may be at least 10%, at least 20%, at least 30%, at least 40%, at least 50%, at least 60%, at least 70%, at least 80%, at least 90%, or at least 100% less than the amount of the refractive errors that would have been present without using these methods.

Methods described herein ameliorate refractive errors, including, but not limited to, myopia, hyperopia, astigmatism, presbyopia, pseudophakes (replacing a natural lens with an artificial intraocular lens, for example after cataract surgery), and distortions after laser surgery by administering to at least one eye of a patient a therapeutically effective amount of an ophthalmic preparation comprising one or more parasympathomimetic drugs, or pharmaceutically acceptable salts thereof, and one or more alpha agonists or antagonists, or pharmaceutically acceptable salts thereof.

The present disclosure further provides methods of improving at least one vision parameter in a subject in need thereof, comprising administering to the subject an ophthalmic formulation described herein. As used herein, the term "vision parameter" refers to any characteristic in a subject's vision that may be measured and is susceptible to being improved by the ophthalmic formulations and methods described herein. Vision parameters include, but are not limited to, near vision acuity, intermediate visual acuity, distance visual acuity, night vision, day vision, optical aberrations (e.g., glare, light scattering), and uncorrected refractive errors. Additional examples of vision parameters include, without limitation, night time glare, post-LASIK "star burst" glare, visual "halos" seen around light sources, and accommodative insufficiency.

"Improving vision parameter" includes, but is not limited to, near, intermediate, and/or distance visual acuity, and may for example be reflected in the increase of number of letters correctly read at any time point post dosing, the increase in the average letter change, or 2-line or 3-line improvement, all from baseline (i.e., from pre-treatment).

Night vision improvement may be reflected in visual improvement for subjects in dim or dark lighting (e.g., under mesopic or scotopic conditions). Day vision improvement may be reflected in visual improvement for subjects in bright lighting as found during daylight hours or in sunshine (e.g., under photopic conditions). Vision improvement using the methods described herein may also be achieved in combination with or when using other visual aids and devices (e.g., those used for treating myopia or presbyopia), including but not limited to reading glasses, lens modifying medications, and surgical myopic options.

In some aspects, methods of treatment using the ophthalmic formulations described herein result in an at least 2-line improvement from baseline under the condition of photopic, high contrast uncorrected near visual acuity (UNVA). As used herein, the term "photopic" vision is the vision of the eye under well-lit conditions (luminance level 10 to $10^8$ cd/m$^2$). In humans and other animals, photopic vision allows color perception, mediated by cone cells, and a significantly higher visual acuity and temporal resolution than available with scotopic vision (the vision of the eye under low-light conditions; luminance level $10^{-3}$ to $10^{-6}$ cd/m$^2$). As used herein, the term "uncorrected near visual acuity" (UNVA) refers to a subject's ability, without any vision aid (such as eyeglasses or contact lenses), to see the details of objects within arm's distance from the body (e.g., at 33-41 cm away from the eye).

In some aspects, methods of treatment using the ophthalmic formulation described herein result in an at least 3-line improvement from baseline under the condition of photopic, high contrast UNVA. In other aspects, methods described herein result in an increase in the average letter change from baseline under the condition of photopic, high contrast UNVA.

The term "improvement from baseline" refers to the increase from pre-treatment in the number of letters correctly read at certain post treatment time point. As used herein, the term "2-line improvement from baseline" or "3-line improvement from baseline" or similar improvement from baseline refers to a subject's ability to read 2 or 3 more lines of letters on a standard chart (e.g., Snellen, ETDRS, Logarithmic Visual Acuity Chart, etc.) after treatment with a topical ophthalmic composition of the invention when comparing to the number of lines readable before treatment.

In some aspects, methods of treatment using the ophthalmic formulations described herein result in an at least 2-line improvement from baseline under the condition of mesopic, high contrast UNVA. As used herein, the term "mesopic" vision refers to a combination of photopic vision and scotopic vision in low but not quite dark lighting situations. Mesopic light levels range from luminances of approximately 0.001 to 3 cd/m$^2$. Most night-time outdoor and traffic lighting scenarios are in the mesopic range. The human eye uses scotopic vision under low-light conditions and mesopic vision in intermediate conditions. Humans see differently at different light levels. This is because under high light levels typical during the day (photopic vision), the eye uses cones to process light. Under very low light levels, corresponding to moonless nights without electric lighting (scotopic vision), the eye uses rods to process light. At many nighttime levels, a combination of both cones and rods supports vision. Photopic vision facilitates excellent color discrimination ability, whereas colors are indiscriminable under scotopic vision. Mesopic vision falls between these two extremes. In most night time environments, there is enough ambient light at night to prevent true scotopic vision.

In some aspects, methods of treatment using the topical ophthalmic compositions described herein result in an at least 3-line improvement from baseline under the condition of mesopic, high contrast UNVA. In other aspects, methods described herein result in an increase in the average letter change from baseline under the condition of mesopic, high contrast UNVA.

In some aspects, methods of treatment using the ophthalmic formulations described herein result in an at least 2-line improvement from baseline under the condition of photopic, high contrast uncorrected distance visual acuity (UDVA). As used herein, the term "uncorrected distance visual acuity" (UDVA) refers to a subject's ability, without any vision aid (such as eyeglasses or contact lenses), to see the details of objects beyond arm's distance from the body (e.g., greater than 4 meters away from the eye).

In some aspects, methods of treatment using the ophthalmic formulations described herein result in an at least 3-line improvement from baseline under the condition of photopic, high contrast UDVA. In other embodiments, methods described herein result in an increase in the average letter change from baseline under the condition of photopic, high contrast UDVA.

In some aspects, methods of treatment using the ophthalmic formulations described herein result in an at least 2-line improvement from baseline under the condition of mesopic, high contrast distance-corrected near visual acuity (DCNVA). As used herein, the term "distance corrected near visual acuity" (DCNVA) refers to a subject's ability to see the details of objects within arm's distance from the body (e.g., at 33-41 cm away from the eye), with the use of vision aids such as eyeglasses or contact lenses that correct for distance vision issues.

In some aspects, methods of treatment using the ophthalmic formulations described herein result in an at least 3-line improvement from baseline under the condition of mesopic, high contrast DCNVA. In other aspects, methods described herein result in an increase in the average letter change from baseline under the condition of mesopic, high contrast DCNVA. In yet other aspects, methods described herein result in an at least 3-line improvement from baseline under the condition of photopic, high contrast DCNVA. In additional aspects, methods described herein result in an at least 2-line improvement from baseline under the condition of photopic, high contrast DCNVA. In further aspects, methods described herein result in an increase in the average letter change from baseline under the condition of photopic, high contrast DCNVA.

In certain aspects, methods of treatment using the ophthalmic formulations described herein result in an at least 2-line improvement from baseline under the condition of mesopic, high contrast distance-corrected intermediate visual acuity (DCIVA). As used herein, the term "distance-corrected intermediate visual acuity" (DCIVA) may be used to refer to a subject's ability to see the details of objects at intermediate distances with the use of vision aids such as eyeglasses or contact lenses that correct for distance vision issues.

In some aspects, methods of treatment using the ophthalmic formulations described herein result in an at least 3-line improvement from baseline under the condition of mesopic, high contrast DCIVA. In other aspects, methods described herein result in an increase in the average letter change from baseline under the condition of mesopic, high contrast DCIVA. In yet other aspects, methods described herein result in an at least 2-line improvement from baseline under the condition of photopic, high contrast DCIVA. In additional aspects, methods described herein result in an at least 3-line improvement from baseline under the condition of photopic, high contrast DCIVA. In further aspects, methods described herein result in an increase in the average letter change from baseline under the condition of photopic, high contrast DCIVA.

Processes for Preparing Ophthalmic Formulations

The present disclosure also provides processes for preparing ophthalmic formulations comprising carbachol.

In some aspects, an ophthalmic formulation comprising from about 1 wt % to about 4 wt % carbachol, or a pharmaceutically acceptable salt thereof, from about 0 wt % to about 1 wt % of one or more viscosity agents, from about 0.01 wt % to about 0.02 wt % of one or more tonicity agent, and from about 0.05 wt % to about 1 wt % of one or more buffers, wherein the pH of the formulation is from about 7 to about 7.6, is prepared by a process comprising adding carbachol, or a pharmaceutically acceptable salt thereof, one or more tonicity agents, and one or more viscosity agents to water and mixing to provide the formulation.

In some aspects, the buffer is a phosphate buffer. In some aspects, the phosphate buffer comprises sodium phosphate monobasic monohydrate and sodium phosphate dibasic heptahydrate.

In some aspects, the one or more viscosity agents is HPMC.

In some aspects, the one or more tonicity agents is sodium chloride.

In some aspects, the process comprises adding benzalkonium chloride.

In some aspects, the process comprises adding sodium chloride.

In some aspects, the process comprises adding hydrochloric acid.

In some aspects, the process comprises adding sodium hydroxide.

In some aspects, the ophthalmic formulation is aseptically filled into vials.

In some aspects, each vial is filled with from about 0.01 g to about 0.1 g, from about 0.05 g to about 0.15 g, from about 0.2 g to about 0.4 g, from about 0.3 g to about 0.5 g, from about 1 g to about 2 g, from about 1.5 g to about 2.5 g, from about 2.5 g to about 3.5 g, from about 3 g to about 4 g, or from about 3.5 g to about 5 g of the ophthalmic formulation.

In some aspects, each vial is filled with from about 0.1 g to about 0.3 g of the ophthalmic formulation.

In some aspects, each vial is filled with from about 2 g to about 2.7 g of the ophthalmic formulation.

The following examples are illustrative and do not limit the scope of the claimed aspects.

EXAMPLES

Example 1

3% Carbachol Formulation

Table 1 lists an exemplary ophthalmic formulation comprising 3% carbachol that was tested.

TABLE 1

| 3% Carbachol Formulation | | |
| --- | --- | --- |
| Component | Grade | Formulation 1 Concentration (wt %) |
| Carbachol | USP | 3% |
| Sodium Carboxymethyl Cellulose | USP/Ph Eur | NA |
| Hydroxypropylmethyl Cellulose (HPMC) - | USP/Ph Eur | 1% |
| Benzalkonium Chloride | NF/Ph Eur | 0.01% |

Example 2

Additional Exemplary Carbachol/Brimonidine Formulations

Table 2 lists exemplary ophthalmic formulations comprising carbachol with and without brimonidine that were prepared for further testing.

TABLE 2

| Additional Carbachol/Brimonidine Formulations | | | | | |
| --- | --- | --- | --- | --- | --- |
| | | | Formulation #: | | |
| Component | Grade | Function | 2 Concentration (wt %) | 3 Concentration (wt %) | 4 Concentration (wt %) |
| Carbachol | USP | Active | 2.75% | 2.75% | 2.75% |
| Brimonidine Tartrate | House | Active | 0.1% | 0.1% | NA |
| Hydroxypropylmethyl Cellulose (HPMC) | USP | Viscosity agent | 0.2% | 0.2% | 0.2% |
| Benzalkonium Chloride | NF | Penetration enhancer | 0.01% | NA | NA |
| Sodium Chloride | USP | Tonicity adjuster | NA | NA | 0.013% |
| Sodium Phosphate Monobasic Monohydrate | USP | Buffer | 0.00171% | 0.00171% | 0.0232% |
| Sodium Phosphate Dibasic Heptahydrate | USP | Buffer | 0.332% | 0.332% | 0.290% |

TABLE 2-continued

Additional Carbachol/Brimonidine Formulations

| | | | Formulation #: | | |
|---|---|---|---|---|---|
| | | | 2 | 3 | 4 |
| Component | Grade | Function | Concentration (wt %) | Concentration (wt %) | Concentration (wt %) |
| Hydrochloric Acid/Sodium Hydroxide (IN stock solutions) | NF | pH adjuster | QS to pH 7.4 | QS to pH 7.4 | QS to pH 7.4 |
| Purified Water | USP | Solvent | QS to 100% | QS to 100% | QS to 100% |

Example 3

Mean Change in Pupil Size and NVA in Phakic Emmetropic Presbyopes

This study compared the efficacy of a formulation containing both carbachol and brimonidine with separate formulations of carbachol and brimonidine being administered at the same time. The same participants received the combination formulation and the separate formulations, with a one week washout period between the administrations.

The study tested and compared in a blind study the effectiveness of using a parasympathomimetic drug (3% carbachol) and an alpha agonist (0.2% brimonidine) in both combined and separate forms to create optically beneficial miosis to pharmacologically improve vision in presbyopia.

A prospective, blind, randomized clinical trial utilized ten naturally emmetropic and presbyopic subjects between 42 years and 58 years old with an uncorrected distance visual acuity of at least 20/20 in both eyes without additional ocular pathology. Participants were volunteers selected at random. Presbyopia is considered present if an uncorrected end-point print size ≥Jaeger (J) improved by ≥1 optotype with the use of a lens ≥+1.00 D. All subjects were in good physical and ocular health and completed a questionnaire to ascertain any contraindications for participation or predisposition to complications (e.g. heart or respiratory conditions, migraines, high myopia, ocular or systemic medications, or ocular surgeries). All subjects had a fully dilated eye examination before they were considered eligible for the study. The examination screened for contraindications to the drugs, susceptibility to retinal detachment, ocular pathology, or peripheral retinal degeneration.

The inclusion criteria included age between 41 and 60 years, presbyopia (uncorrected end-point print size ≥Jaeger (J) 5 improved by ≥1 optotype with the use of a lens ≥+1.00 D), emmetropia (cycloplegic spherical equivalent (SE), ±0.25 D; 20 astigmatism, ≤0.25 D) and binocular uncorrected distance visual acuity ≥20/20. Exclusion criteria included patients with myopia, hyperopia and astigmatism which is higher than 0.25 diopter, and corneal, lens, vitreous opacities, pupil irregularities, anisocoria, amblyopia, chronic general pathologies and medications that would interact unfavorably with carbachol and brimonidine.

All subjects received a single dose 3% carbachol and 0.2% brimonidine in both combined and separate forms in their non-dominant eye in a crossover manner with one week washout between tests. In the separate form, carbachol was administered first followed by brimonidine after 5 minutes. The subjects' pupil size and both near and distance visual acuities were evaluated pre- and post-treatment at 1, 2, 4, and 8 hours, by a 30 masked examiner at the same room illumination. Additionally, all subjects received just a single dose of 3% carbachol or just a dose of 0.2% brimonidine.

The study used standard Snellen projector chart to measure distance visual acuity. Near visual acuity was assessed at 40 cm using Jaeger (J) Eye Chart. Statistical analysis was performed using the Student's t-test and p value of less than 0.05 was considered statistically significant. Data was expressed as mean, range, and standard deviation (SD).

Figure 1B:
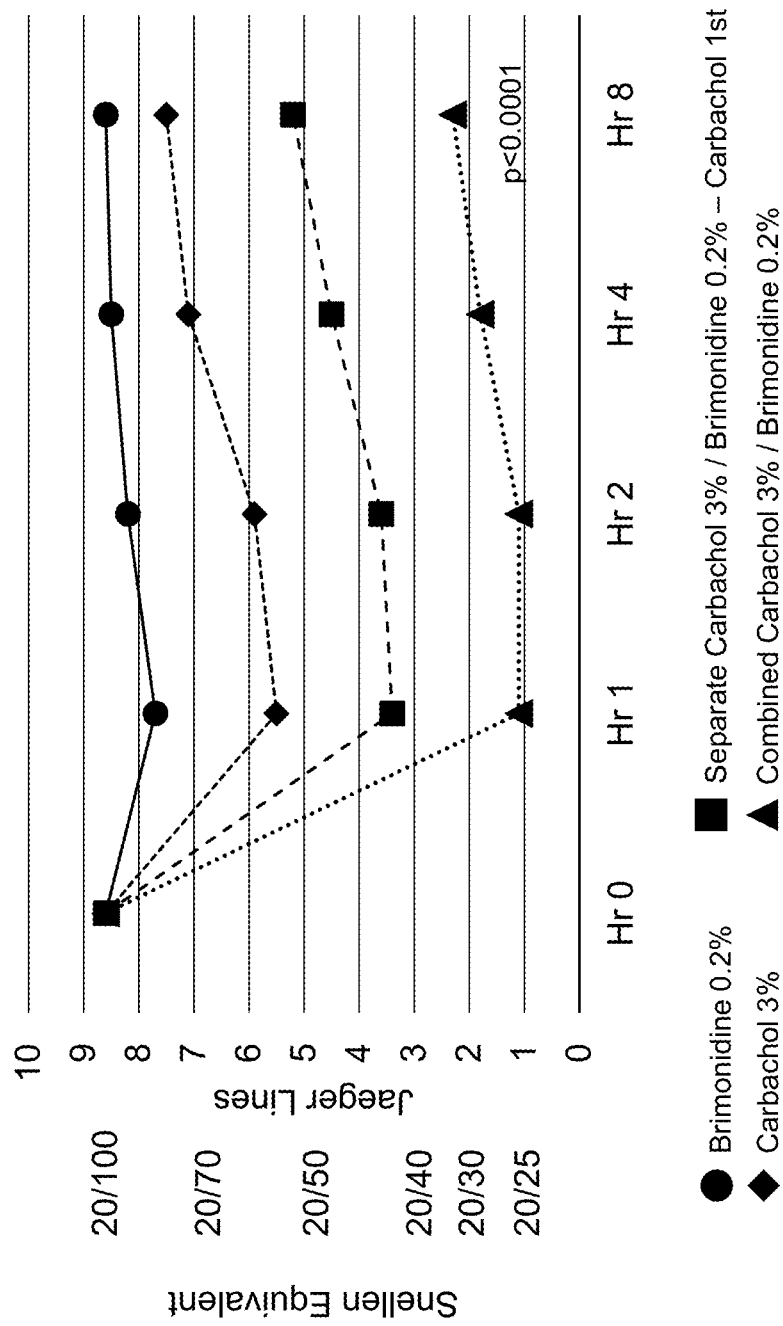

FIGS. 1A and 1B show a comparison of the distribution of mean change in pupil size (mm) and NVA in phakic emmetropic presbyopes over time (8 hours) between brimonidine/carbachol combination drops, separately administered drops, brimonidine alone, and carbachol alone. The mean change in pupil size is the least in participants treated with 0.2% brimonidine alone, and the most in patients treated with the 0.2% brimonidine/3% carbachol combination.

The combination drops had a synergistic effect, improving near visual acuity better than the carbachol and brimonidine administered separately.

Example 4

Mean Change from Baseline in Bilateral Uncorrected Near Visual Acuity (BUCNVA) in Phakic or Pseudophakic Emmetropic Presbyopes This study compared the safety, tolerability and efficacy of three ophthalmic solutions containing 2.75 wt % carbachol with or without brimonidine, and with or without benzalkonium chloride.

Figure 2:
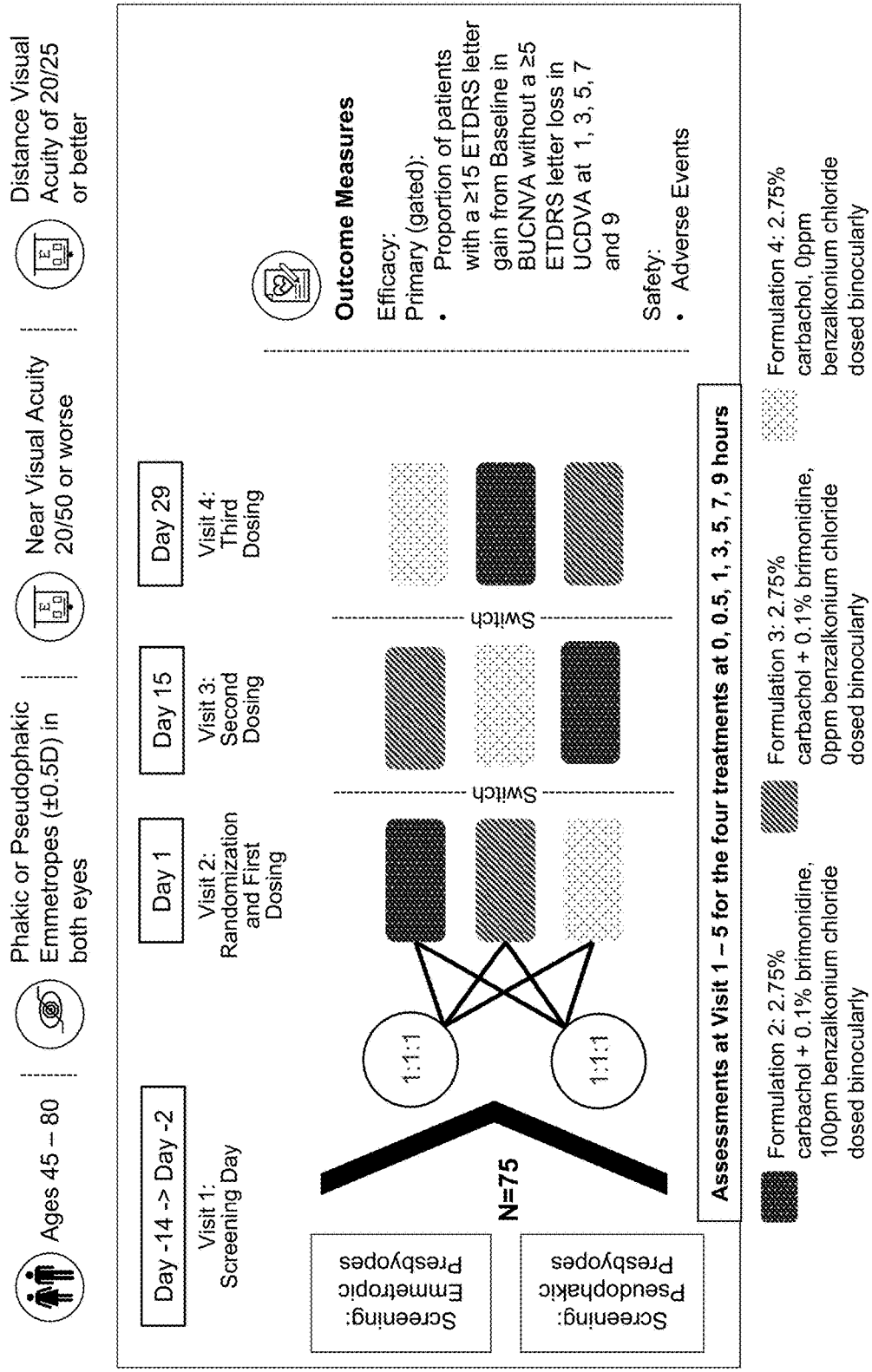
FIG. 2 shows the design and exclusion criteria of the Phase 2 Crossover Study of the safety, tolerability and efficacy of Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride).

FIG. 2 shows the design and exclusion criteria of the Phase 2 Crossover Study of the safety, tolerability and efficacy of Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride).

Figure 3:
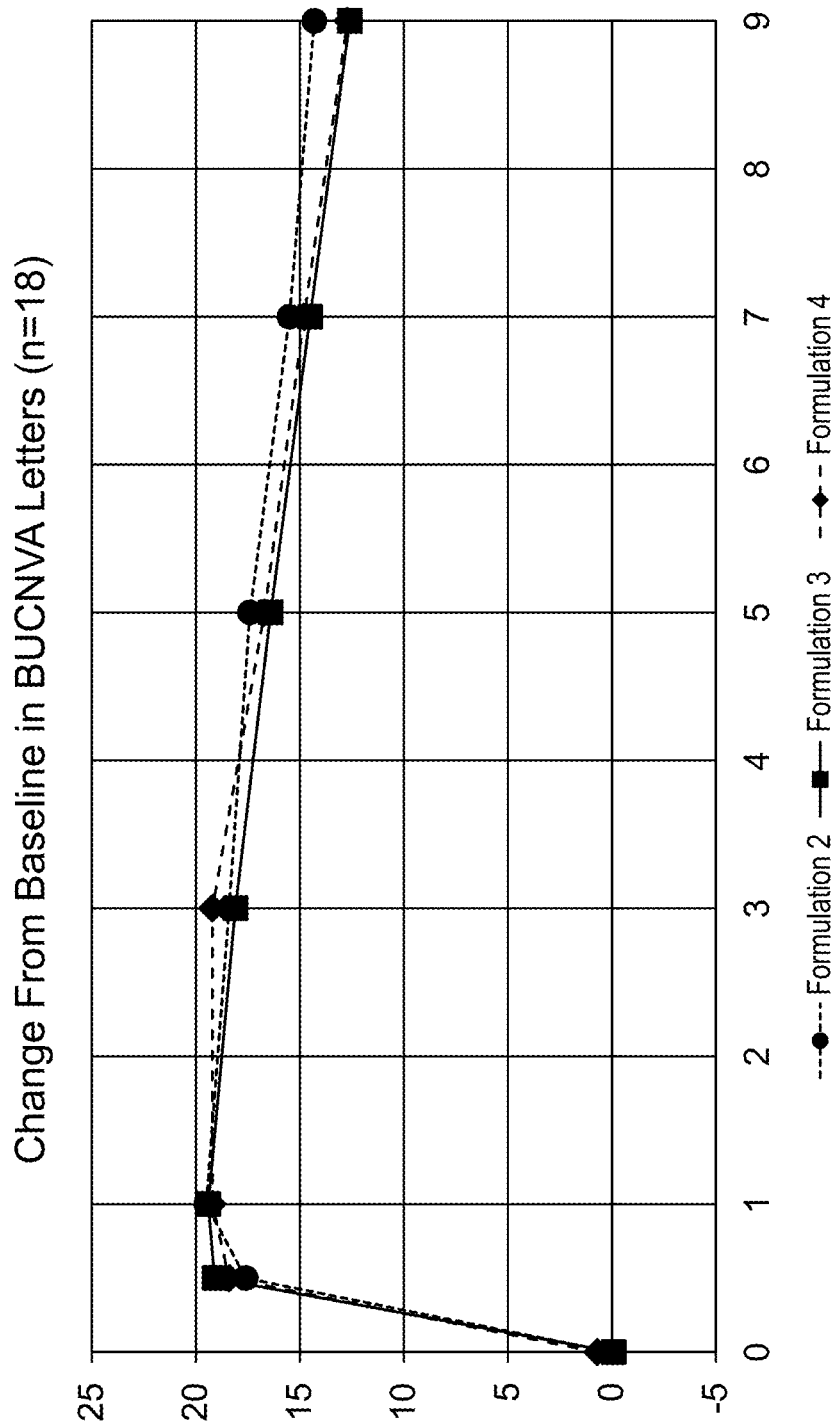
FIG. 3 shows the change from baseline in bilateral uncorrected near visual acuity (BUCNVA) letters over time (9 hours) between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

FIG. 3 shows a comparison of the distribution of change from baseline in bilateral uncorrected near visual acuity (BUCNVA) letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

Figure 4:
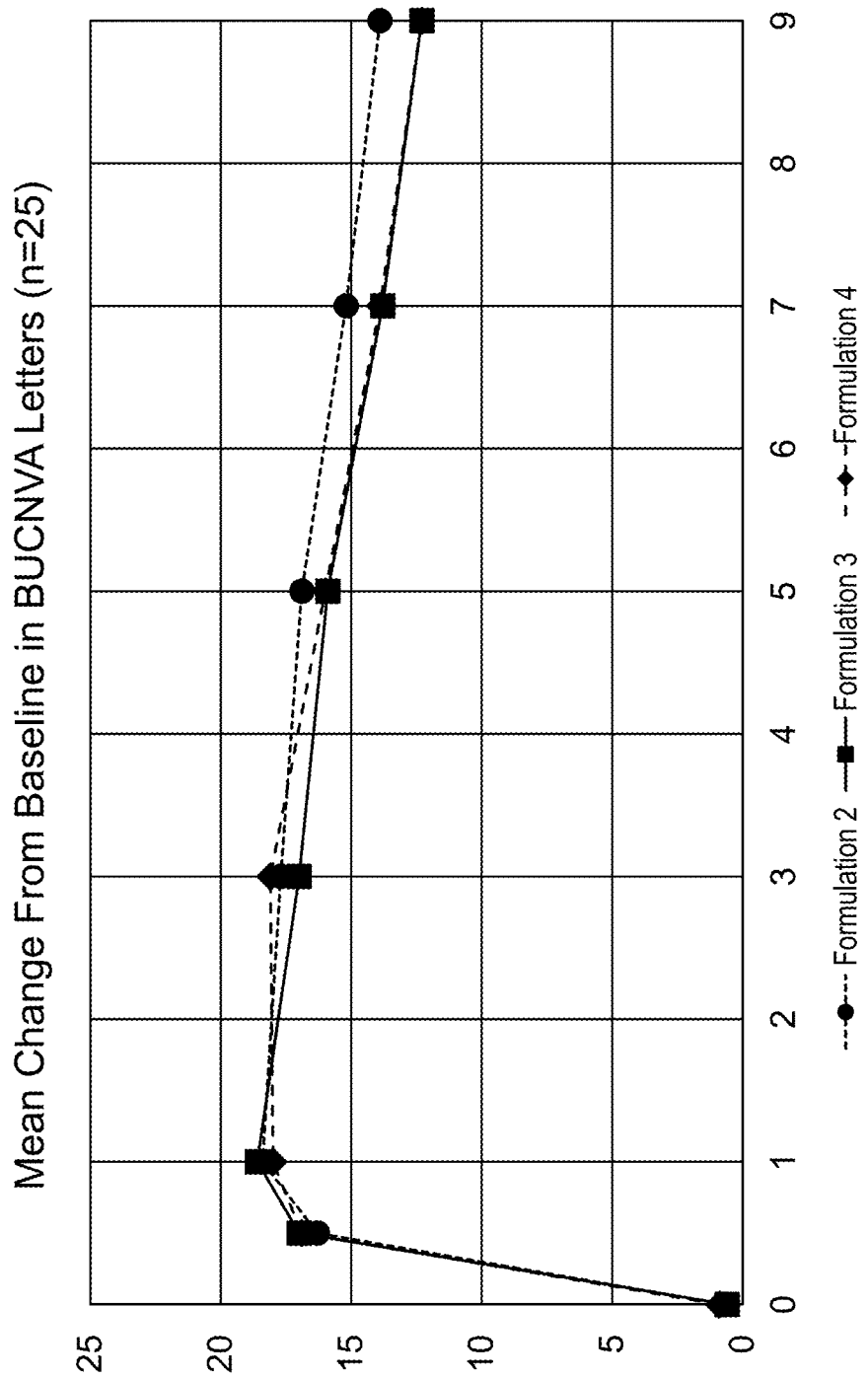
FIG. 4 shows the mean change from baseline in BUCNVA letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 25 subjects.

FIG. 4 shows a comparison of the distribution of mean change from baseline in BUCNVA letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 25 subjects.

Figure 5:
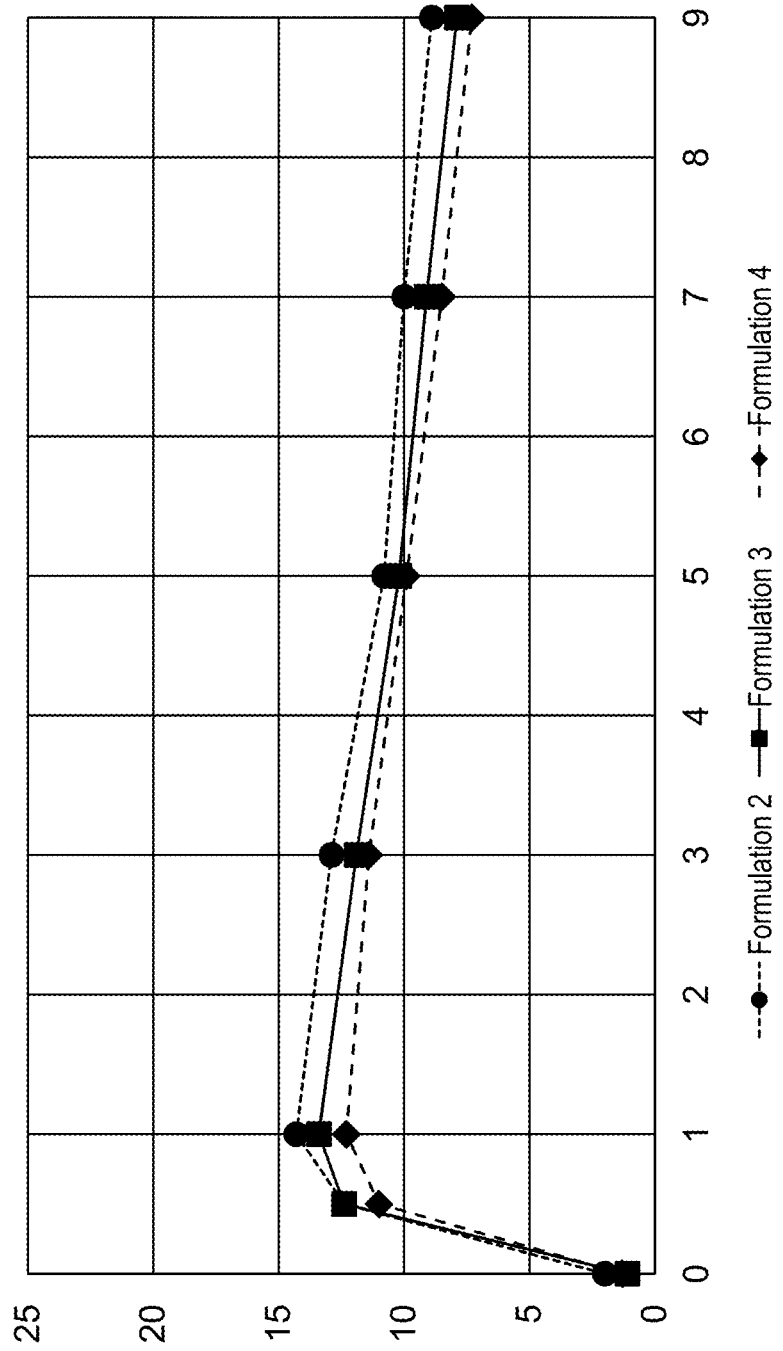
FIG. 5 shows the change from baseline in BUCNVA letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 74 subjects.

FIG. 5 shows a comparison of the distribution of change from baseline in BUCNVA letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 74 subjects.

Figure 6:
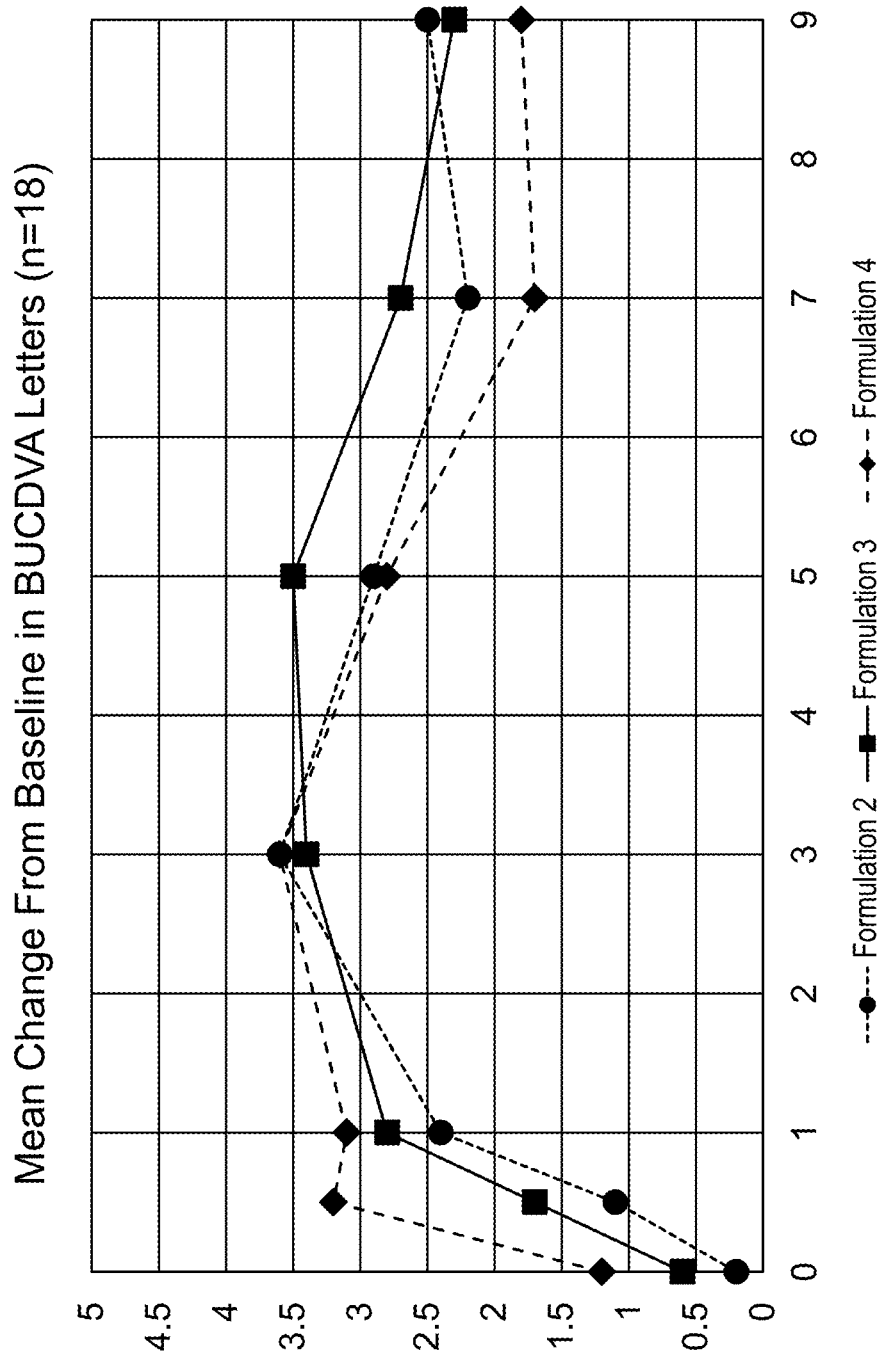
FIG. 6 shows the mean change from baseline in bilateral uncorrected distant visual acuity (BUCDVA) letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

FIG. 6 shows a comparison of the distribution of mean change from baseline in BUCDVA letters over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

Suprisingly, the ophthalmic formulations comprising 2.75 wt % carbachol without benzalkonium chloride demonstrate increased therapeutic effect compared to previous formulations containing 3 wt % carbachol with or without benzalkonium chloride. It was unexpected that formulations comprising 2.75 wt % carbachol performed as well as Formulation 2 (2.75 wt % carbachol and 0.1 wt % brimonidine) and Formulation 3 (2.75 wt % carbachol and 0.1 wt % brimonidine without benzalkonium chloride). Further, fewer active agents could mean fewer side effects and greater patient compliance.

Example 5

Pharmacodynamic Studies in Non-Human Primates (NHP)

Figure 7:
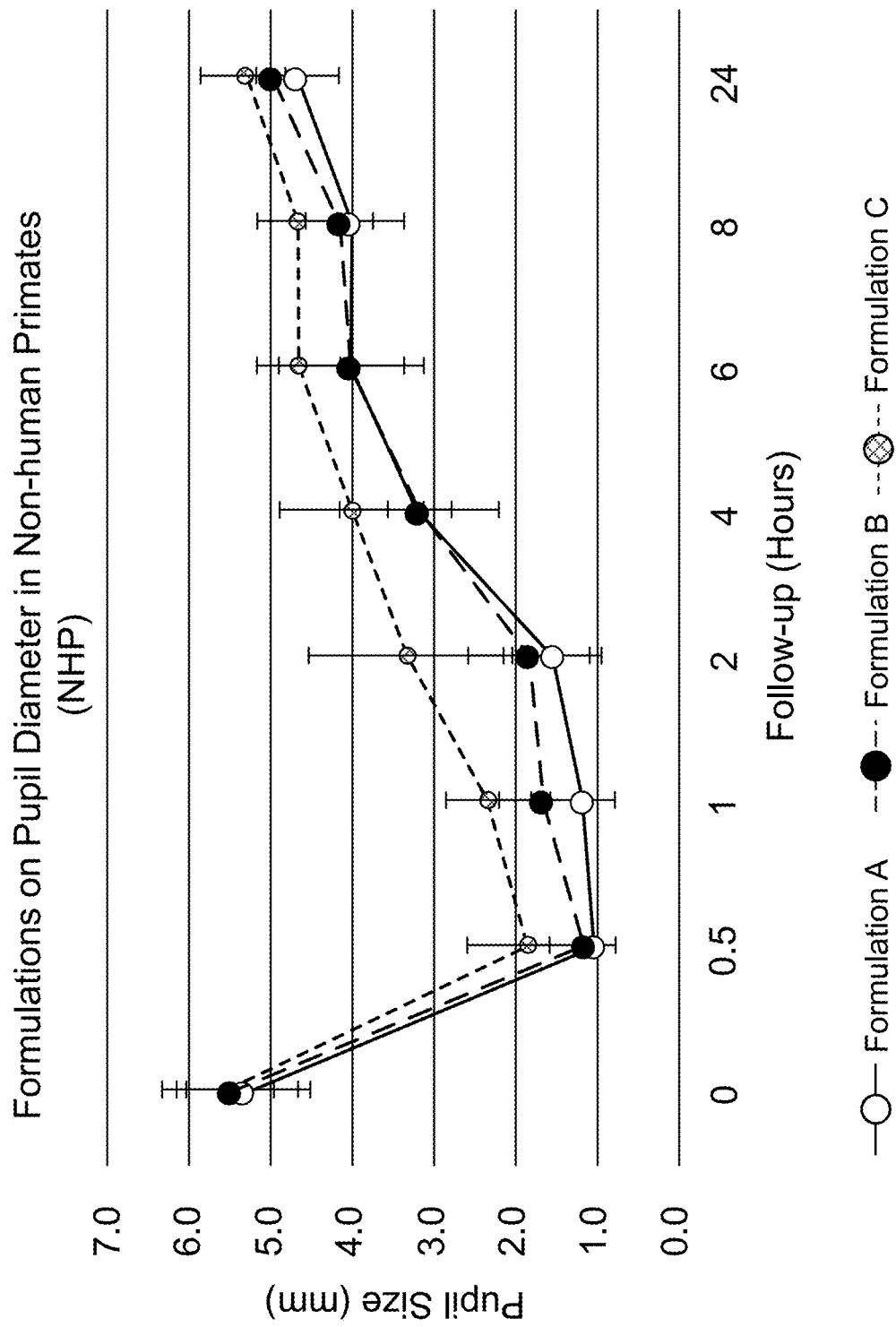
FIG. 7 shows a comparison of the distribution of pupil size (mm) over time (24 hours) between Formulation A (brimonidine/carbachol combination drops with benzalkonium chloride), Formulation B (brimonidine/carbachol combination drops without benzalkonium chloride), and Formulation C (carbachol alone without benzalkonium chloride) in non-human primates (NHP).

FIG. 7 shows a comparison of the distribution of pupil size (mm) over time (24 hours) between Formulation A (brimonidine/carbachol combination drops with benzalkonium chloride), Formulation B (brimonidine/carbachol combination drops without benzalkonium chloride), and Formulation C (carbachol alone without benzalkonium chloride) in non-human primates (NHP).

The combination drops with benzalkonium chloride, the combination drops without benzalkonium chloride, and carbachol alone without benzalkonium chloride were all more active than the 3% carbachol formulation without benzalkonium chloride despite containing a lower concentration of carbachol.

Example 6

Unexpected Availability of Carbachol

Lipophilic compounds will absorb into the aqueous humour by transcorneal permeation. This is driven by a Fickean diffusion process. For the most part extremely hydrophilic compounds and macromolecules gain entry into the eye by conjunctival absorption into the sclera followed by penetration into the iris route or limbus into the aqueous humor. This has a very low bioavailability and is usually considered non-productive absorption.'

The cornea is considered a trilaminate structure relative to mass transfer: an extremely lipophilic epithelium a hydrophilic stroma and the endothelium. The epithelium is 3 to 5 layers thick and has banded tight junctions. It is very liphophilic and has a low permeability to hydrophilic drugs. Penetration begins to optimize at a log D (log distribution coefficient) of 2 to 4. The middle layer, the stroma is 80 to 90% water and acellular. Hydrophilic compounds readily diffuse through the stroma. The inner layer the endothelium is a single layer and poses very little barrier to permeation. Because of the trilaminate nature, drugs must possess sufficient lipophilicity to penetrate the epithelium to be ocularly available across the cornea.

Carbachol is a quaternary amine and highly charged at neutral pH having a pKa of about 15. It has a high solubility of 1 gm/mL and a log P of −3.78 or about 7 units lower than optimal for transcorneal permeation. Carbachol is not expected to have very high corneal permeability on its own. Hence, benzalkonium chloride is usually used to increase the permeability of carbachol in formulations to achieve efficacy. Benzalkonium chloride has been shown to disrupt the corneal epithelium and serve as a permeation enhancer for many drugs. The effect is more pronounced for drugs where the corneal epithelium offers a high resistance to permeation e.g. charge or hydrophilic drugs.

What is surprising from the clinical studies and a NHP study is that a benzalkonium chloride containing formulation and a benzalkonium chloride free formulation (Formulation 2 and Formulation 3, respectively) demonstrate the same pupil response, BUCNVA and duration of effect. Furthermore, is it surprising that while the effect of brimonidine can be seen comparing the response to the Carbachol F and the Brimochol F formulations on pupil response, it is not observed on BUCNVA. Surprisingly, Carbachol alone appears as effective in BUCNVA improvement and duration as both Formulation 2 and Formulation 3. Carbachol would not be expected to have this degree of ocular bioavailability in the absence of benzalkonium chloride. In fact it is usually formulated with benzalkonium chloride for this reason.

Figure 8:
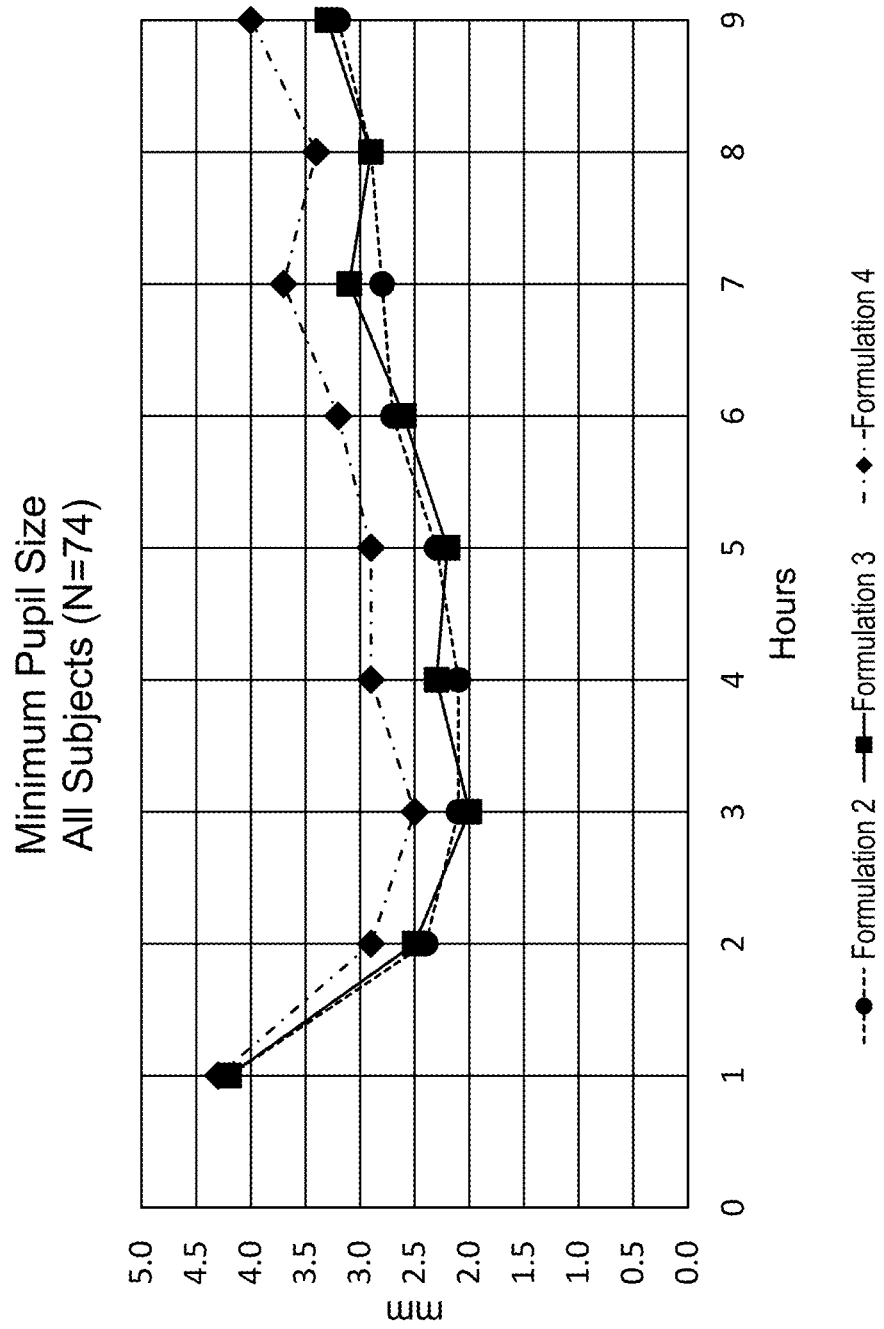
FIG. 8 shows the distribution of minimum pupil size (mm) over time (9 hours) between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 74 subjects.

FIG. 8 shows the distribution of minimum pupil size (mm) over time (9 hours) between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 74 subjects.

Figure 9:
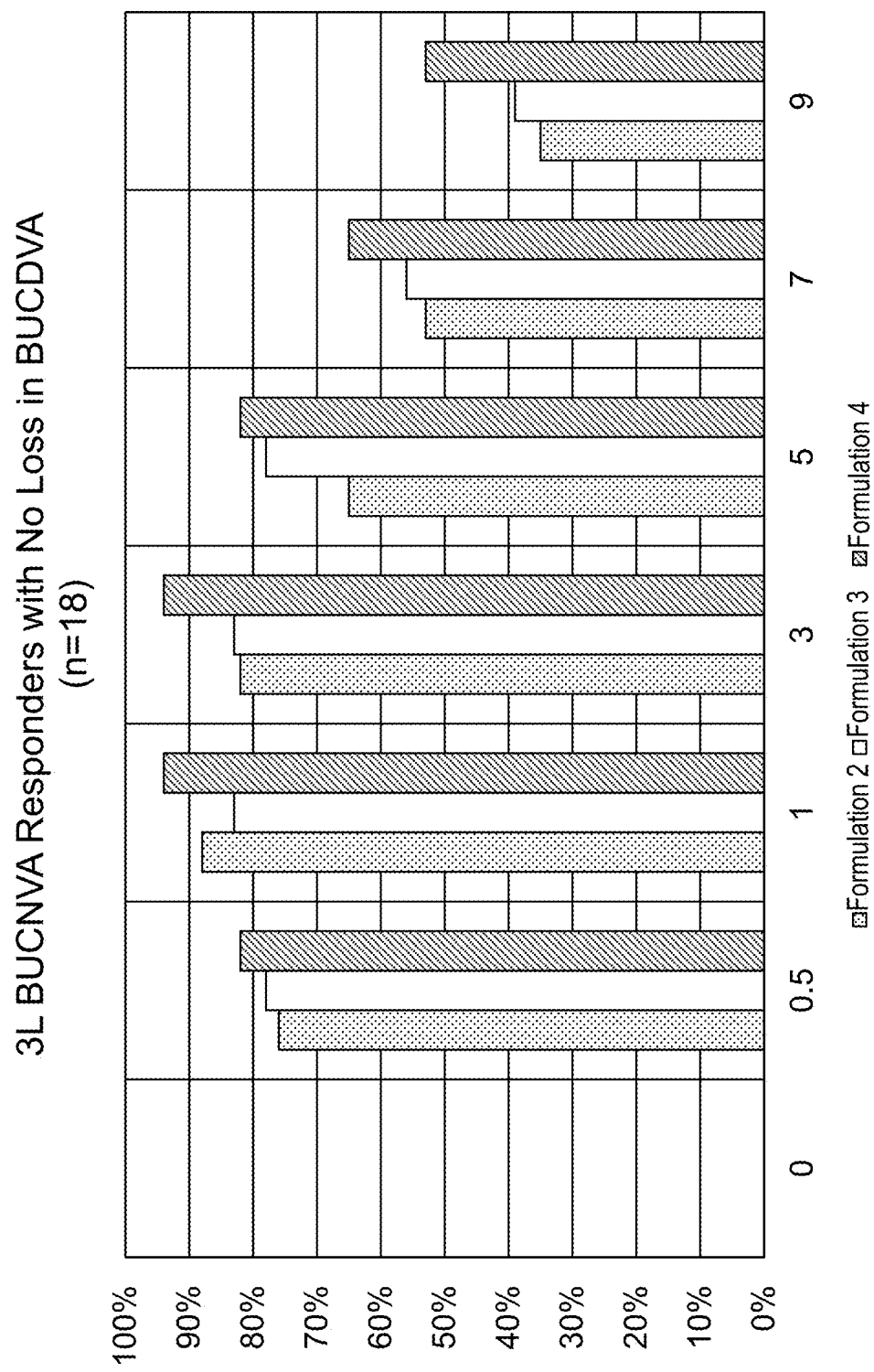
FIG. 9 shows shows a comparison of the distribution of 3 L BUCNVA Responders with no loss in BUCDVA over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

FIG. 9 shows shows a comparison of the distribution of 3 L BUCNVA Responders with no loss in BUCDVA over time between Formulation 2 (2.75 wt % carbachol and 0.1 wt % brimonidine with 0.01 wt % benzalkonium chloride), Formulation 3 (2.75 wt % carbachol and 0.1 wt % brimonidine without benzalkonium chloride), and Formulation 4 (2.75 wt % carbachol without benzalkonium chloride) in 18 subjects.

Example 7

Unexpected Improvement of 0.2% HPMC Formulation Over 1.0% HPMC Formulation (Isopto Carbachol)

Rapid precorneal clearance is one of the major hurdles to productive ocular absorption. Most compounds will penetrate into the eye from topical administration by passive diffusion across the cornea. The driving force for this diffusion is the concentration gradient across the tissue. Hence, any formulation factors that can decrease precorneal clearance and thereby increase the area under the tear film drug concentration versus time curve would be expected to increase ocular bioavailability from a topical drop.

Immediately after dosing the drop undergoes rapid elimination from the precorneal space. The resting cul-de-sac holds about 7 uL, but can hold up to 30 uL. A typical drop is from 35 to 50 uL and as such some of the instilled dose is lost by spilling out of the cul-de-sac and the majority lost by nasolacrimal drainage. Blinking then drives the drop to the puncta followed by nasolacrimal drainage reducing the driving force to transcorneal flux of the applied dose. Precorneal half-life is on the order of minutes, in fact, clearance can be so fast that its only the first blink that spreads drug over the tear film for productive absorption It has been shown that increasing the viscosity of a topical ophthalmic formulation can increase precorneal retention and consequently ocular bioavailability. It has been shown that increasing viscosity can increase topical bioavailability up to a viscosity of about 100 cps with diminishing return after about 15 to 20 cps (Chrai, S. S., & Robinson, J. R. (1974). Ocular evaluation of methylcellulose vehicle in albino rabbits. J Pharm Sci, 63(8), 1218-1223; Patton, T. F., & Robinson, J. R. (1975). Ocular evaluation of polyvinyl alcohol vehicle in rabbits. J Pharm Sci, 64(8), 1312-1316). This relationship has been shown for polyvinyl alcohol and cellulose based viscosifiers.

It is highly unexpected and surprising that in this study isopto carbachol with 1% HPMC has a lower pupil response than 0.2% HPMC formulations. As shown below the pupil response to the 0.2% formulation (Separate carbachol 3%/brimonidine 0.2%) is significantly greater than isopto carbachol. The formulations are essentially the same except that the separate carbachol 3%/brimonidine 0.2% has an HPMC concentration of 0.2% w/v and a viscosity of 3 to 5 cps and isopto carbachol has an HPMC concentration of 1.0%, and would be expected to have a much higher viscosity. Conventional wisdom and the existing data suggests that the performance should be reversed.

Figure 10:
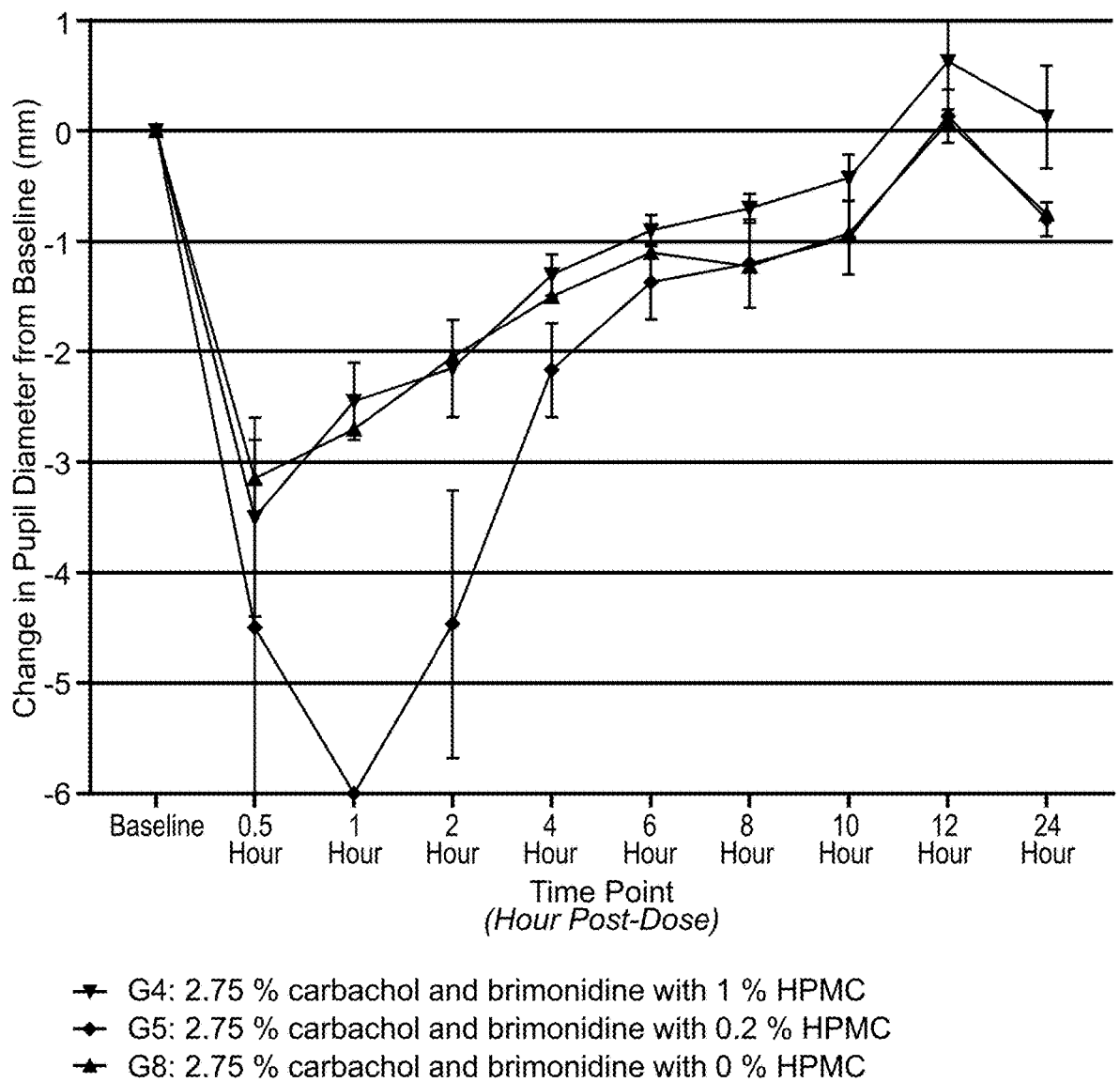
FIG. 10 shows a comparison of the change in pupil size (mm) over time (24 hours) between G4 (2.75% carbachol and brimonidine with 1% HPMC), G5 (2.75% carbachol and brimonidine with 0.2% HPMC), and G8 (2.75% carbachol and brimonidine with 0% HPMC) under scotopic conditions (n=2-4).

FIG. 10 shows a comparison of the change in pupil size (mm) over time (24 hours) between G4 (2.75% carbachol and brimonidine with 1% HPMC), G5 (2.75% carbachol and brimonidine with 0.2% HPMC), and G8 (2.75% carbachol and brimonidine with 0% HPMC) under scotopic conditions.

Figure 11:
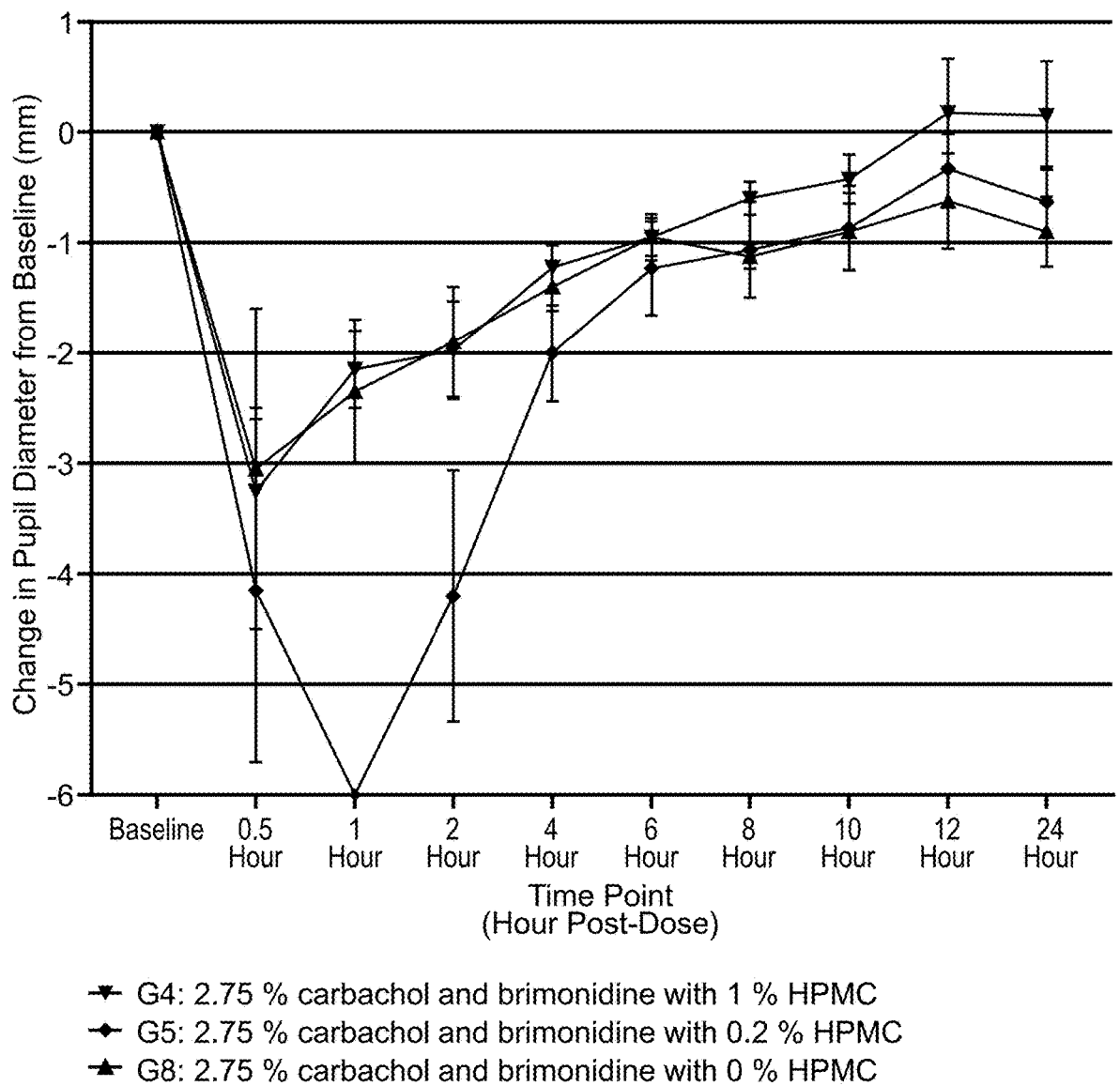
FIG. 11 shows a comparison of the change in pupil size (mm) over time (24 hours) between G4 (2.75% carbachol and brimonidine with 1% HPMC), G5 (2.75% carbachol and brimonidine with 0.2% HPMC), and G8 (2.75% carbachol and brimonidine with 0% HPMC) under mesopic conditions (n=2-4).

FIG. 11 shows a comparison of the change in pupil size (mm) over time (24 hours) between G4 (2.75% carbachol and brimonidine with 1% HPMC), G5 (2.75% carbachol and brimonidine with 0.2% HPMC), and G8 (2.75% carbachol and brimonidine with 0% HPMC) under mesopic conditions.

What is claimed is:

1. An ophthalmic formulation comprising 2.75 wt % carbachol, or a pharmaceutically acceptable salt thereof, 0.1 wt % brimonidine, or a pharmaceutically acceptable salt thereof, 0.2 wt % hydroxypropylmethyl cellulose (HPMC), and a phosphate buffer, wherein the ophthalmic formulation does not contain a preservative.

2. The ophthalmic formulation of claim 1, wherein the phosphate buffer comprises sodium phosphate monobasic monohydrate and sodium phosphate dibasic heptahydrate.

3. The ophthalmic formulation of claim 1, wherein the pH of the formulation is from about 7.2 to about 7.6.

4. The ophthalmic formulation of claim 3, wherein the pH of the formulation is about 7.4.

5. The ophthalmic formulation of claim 1, wherein the brimonidine is brimonidine tartrate.

6. A method for ameliorating or reducing presbyopia in a subject in need thereof comprising administering to at least one eye of the subject the ophthalmic formulation of claim 1.

7. The method of claim 6, wherein the phosphate buffer comprises sodium phosphate monobasic monohydrate and sodium phosphate dibasic heptahydrate.

8. The method of claim 6, wherein the pH of the ophthalmic formulation is from about 7.2 to about 7.6.

9. The method of claim 6, wherein the pH of the ophthalmic formulation is about 7.4.

10. The method of claim 6, wherein the brimonidine is brimonidine tartrate.

11. The method of claim 6, wherein the amelioration or reduction of presbyopia is effective for at least 9 hours.

\* \* \* \* \*